(12) United States Patent
Aronson

(10) Patent No.: US 11,527,332 B2
(45) Date of Patent: *Dec. 13, 2022

(54) SENSOR DATA ANALYZING MACHINES

(71) Applicant: Jeffry David Aronson, Austin, TX (US)

(72) Inventor: Jeffry David Aronson, Austin, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 17/568,083

(22) Filed: Jan. 4, 2022

(65) Prior Publication Data

US 2022/0130555 A1 Apr. 28, 2022

Related U.S. Application Data

(63) Continuation-in-part of application No. 17/165,191, filed on Feb. 2, 2021, now Pat. No. 11,238,992, which
(Continued)

(51) Int. Cl.
*G16H 50/70* (2018.01)
*G16H 50/20* (2018.01)
(Continued)

(52) U.S. Cl.
CPC ........... *G16H 50/70* (2018.01); *A61B 5/0077* (2013.01); *A61B 5/0205* (2013.01); *G06N 20/00* (2019.01); *G16H 50/20* (2018.01)

(58) Field of Classification Search
CPC ...... G16H 50/70; G16H 50/20; A61B 5/0077; A61B 5/0205; G06N 20/00
See application file for complete search history.

(56) References Cited

U.S. PATENT DOCUMENTS

2009/0067686 A1* 3/2009 Bosh ..................... G06V 40/12
382/124
2011/0040574 A1* 2/2011 Fung ..................... H04L 9/3247
713/168
(Continued)

OTHER PUBLICATIONS

Elliott et al., "Expanding the Human-Biometric Sensor Interaction Model to Identity Claim Scenarios", Mar. 2015, IEEE International Conference on Identity, Security and Behavior Analysis, pp. 1-6 (Year: 2015).*

*Primary Examiner* — Kenneth W Chang
(74) *Attorney, Agent, or Firm* — John A. Fortkort; Fortkort & Houston PC

(57) ABSTRACT

Scalable, configurable, universal, complete spectrum sensor data analyzing machines are provided that make selected determinations from a complete spectrum of cyber determinations regarding or utilizing sensor observations or sensor observation subjects. Analyzing machines utilize necessary resources and predetermined criteria in their making of selected cyber determinations. Analyzing machines utilize measure points in their accurate locating of selected analytically rich aspects, characteristics, or features of or from sensor observation-derived representations, analyzing machines assign appropriate informational representations to selected analytically rich aspects, characteristics, features, or measure points, which are stored in concise datasets where they can be utilized in real-time or thereafter by analyzing machines in their making of selected cyber determinations regarding or utilizing sensor observations or sensor observation subjects. Analyzing machines are configurable for being utilized, in whole or part, as touchless user interfaces, 100% accurate, constantly performed cyberspace identity tests, or universal health metrics monitors.

26 Claims, 1 Drawing Sheet

Related U.S. Application Data is a continuation-in-part of application No. 16/891,080, filed on Jun. 3, 2020, now Pat. No. 10,943,693, which is a continuation-in-part of application No. 15/981,785, filed on May 16, 2018, now Pat. No. 10,943,097.

(60) Provisional application No. 62/507,128, filed on May 16, 2017.

(51) Int. Cl.
*A61B 5/0205* (2006.01)
*A61B 5/00* (2006.01)
*G06N 20/00* (2019.01)

(56) References Cited

U.S. PATENT DOCUMENTS

| | | | |
|---|---|---|---|
| 2011/0282168 A1* | 11/2011 | Weiss | A61B 5/7465 600/323 |
| 2012/0096549 A1* | 4/2012 | Amini | H04L 63/1433 726/23 |
| 2016/0051169 A1* | 2/2016 | Hong | A61B 5/02427 600/595 |

* cited by examiner

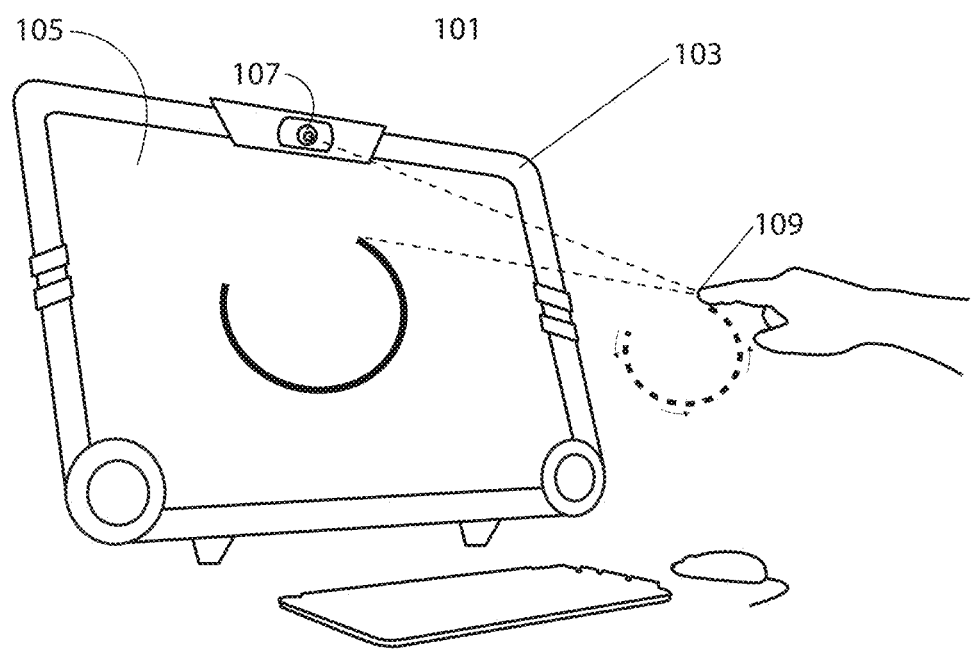

SENSOR DATA ANALYZING MACHINES

CROSS-REFERENCE TO RELATED APPLICATIONS

This application is a continuation-in-part application of U.S. patent application Ser. No. 17/165,191, filed Feb. 2, 2021, entitled "Configurable Concise Datasets Platform", having the same inventor, now allowed, which is incorporated herein by reference in its entirety; which application is a continuation-in-part application of U.S. patent application Ser. No. 16/891,080, filed Jun. 3, 2020, issued as U.S. Pat. No. 10,943,693 on Mar. 9, 2021, entitled "Concise Datasets Platform", having the same inventor, which is incorporated herein by reference in its entirety; which application is a continuation-in-part application of U.S. patent application Ser. No. 15/981,785, filed May 16, 2018, issued as U.S. Pat. No. 10,943,097 on Mar. 9, 2021, entitled "Scalable Configurable Universal Full Spectrum Cyber Process That Utilizes Measure Points From Sensor Observation-Derived Representations or Analytically Rich Sparse Data Sets For Making Cyber Determinations Regarding or Utilizing Sensor Observations or Sensor Observation Subjects", having the same inventor, which is incorporated herein by reference in its entirety; which application claims the benefit of priority from U.S. provisional application No. 62/507,128, entitled "Scalable Universal Full Spectrum Cyber Determining Process That May Utilize Reference Points Located On Sensor-Observation-Derived Representations", having the same inventor, which was filed May 17, 2017, and which is incorporated herein by reference in its entirety.

FIELD OF THE DISCLOSURE

The present disclosure relates generally to one or more machines that utilize tools, methodologies, programming, devices, measure points, and concise datasets in their making of selected cyber determinations regarding or utilizing sensor observations or sensor observation subjects, and more particularly to scalable, configurable, universal, full spectrum, sensor data analyzing machines that are configurable for utilizing resources, including computers, tools, methodologies, programming, information, data, selected criteria, and measure points for selecting, deriving, or utilizing data for or from concise datasets, wherein analyzing machines utilize the concise datasets in their making of selected cyber determinations from a complete spectrum of cyber determinations that can be made regarding or utilizing sensor observations or sensor observation subjects.

BACKGROUND OF THE DISCLOSURE

Prior art machines for providing cyber determinations regarding, or utilizing sensor observations or sensor observation subjects cannot answer the world's ever-increasing needs for machines that quickly, efficiently, accurately, and reliably make any cyber determinations from a complete spectrum of cyber determinations that can be made regarding or utilizing sensor observations or sensor observation subjects.

A few examples of needs for machines that make cyber determinations regarding or utilizing sensor observations or sensor observation subjects that are not being met by prior art include: (a) machines that constantly make accurate or reliable real-time cyber determinations regarding any one specific person's identity, (b) machines that provide a complete spectrum of real-time cyber determinations that are used for a complete spectrum of sensor observation-derived operations of autonomous vehicles or other autonomous devices, (c) machines that provide accurate or reliable cyber determinations that are used for medical diagnoses or that are used in the making of medical diagnoses, (d) machines that are used in the providing of real-time cyber determinations that any one specific person has an imminent intent to do harm, (e) machines that are used in the providing of real-time cyber determinations regarding precisely what people are looking at, or (f) machines that are used in the providing of cyber determinations regarding the state of a specific person's mental or physical health.

SUMMARY OF THE DISCLOSURE

Unless otherwise specified herein, throughout this entire disclosure, use of any singular form of any word, phrase, or statement indicates either the singular or the plural form of the word, phrase, or statement, and use of any plural form of any word, phrase, or statement indicates either the singular or the plural form of the word, phrase, or statement. Additionally, the term "or" shall be construed as the logically inclusive "or". Hence, the statement "A or B" shall be true if: (a) only A is true, (b) only B is true, and (c) both A and B are true; the notation "A and/or B" explicitly refers to the logically inclusive "or".

Prior art sensor data analyzing machines do not answer current needs for the simple, efficient, accurate, or reliable making of selected cyber determinations regarding or utilizing sensor observations or sensor observation subjects.

Further, prior art does not answer current needs for sensor data analyzing machines that are utilizable in the making of a complete spectrum of cyber determinations regarding or utilizing a complete spectrum of sensor observations or a complete spectrum of sensor observation subjects.

The disclosed scalable, configurable, universal, complete spectrum sensor data analyzing machines are configurable for utilizing data from sensor observations in their answering of selected questions (their making of selected cyber determinations) regarding or utilizing sensor observations or sensor observation subjects.

Analyzing machines are configurable for utilizing measure points in their locating of selected analytically rich aspects, characteristics, or features of or from sensor observation-derived representations of sensor observations or sensor observation subjects.

When the questions to be answered by analyzing machines have been selected, then determinations are made regarding which analytically rich aspects, characteristics, or features of or from sensor observation-derived representations can, or will be used for accurately or reliably answering or aiding in the answering of the selected questions.

Analyzing machines are configurable for answering selected questions regarding or utilizing sensor observations or sensor observation subjects through utilization of: (a) information, (b) data from sensor observations, or (c) data that were derived from the processing of information or data from sensor observations.

Using data from a video camera that is configured to observe the face of a driver of a vehicle as an example, analyzing machines are configurable for answering questions regarding this one sensor observation subject. In the case of this example, the question is: Has the driver of a vehicle fallen asleep?

Analyzing machines are configurable for utilizing only two measure points that are located on sensor observation-derived representations of a vehicle driver's face for continuously answering the above question as concisely or efficiently as possible. One measure point locates the image sensor observation-derived representation of the bottom center of the left upper eyelid and the second measure point locates the image sensor observation-derived representation of the top center of the lower eyelid of the same eye.

Analyzing machines are configurable for assigning appropriate standard informational representations regarding, or utilizing each of the two selected measure points. Wherein, analyzing machines are further configurable for selecting the X, (horizontal), or the Y (vertical) line locations where each measure point will be located on pixel grids of sensor observation-derived representations. Data that represents the distance between the two measure points, if any, are used by analyzing machines to determine if a person's eyelids are closed during any number of sequential video images.

Should the horizontal lines on which both of the measure points are located on drop down together for at least a selected number of lines, over a selected number of sequential video images, then the data regarding changes in the horizontal line location are utilizable by analyzing machines in their making of cyber determinations that a driver's head has dropped a specific distance and at a specific rate of drop. Data regarding the distance and rate of drop of the driver's head, along with data regarding the duration of time that the driver's eyelids have been closed can be used by analyzing machines in their accurate or reliable making of cyber determinations that drivers of vehicles have fallen asleep.

Working concise datasets from the previous example include data regarding only two pixels from the over two million pixels of each 1080p video-formatted image. Data regarding the two pixels can easily be used by analyzing machines in their answering of the selected question: Has the driver of the vehicle fallen asleep? This is a simple question that prior art machines are not able to efficiently or reliably answer, due, at least in part, to prior art's use of far more complex tools, methodologies, or programming in their attempts to accurately or reliably answer selected questions. Further, utilization of analyzing machines and their resources reduces the size of original image sensor observation datasets regarding over two million pixels per image to much smaller simple or efficient working concise datasets that are comprised of data regarding the X and the Y line locations of only two pixels per image. This results in a one-million-to-one reduction in the size of the working datasets that are used by analyzing machines in their answering of the selected question. Further, since the selected question is accurately or reliably answered using data regarding only two pixels per sequential video image, then the remainder of the pixels that are used by prior art could be considered to be confusing or unnecessary noise.

Analyzing machines are configurable for employing tools, methodologies, or programming from a complete spectrum of tools, methodologies, or programming that can be utilized by analyzing machines in their making of selected cyber determinations regarding or utilizing what has been observed at the points where measure points have been located on sensor observation-derived representations. In the case of this example, analyzing machines are configurable for utilizing concise datasets regarding only two eyelid representation-located measure points, wherein analyzing machines utilize only the X and the Y line locations of the two measure points from each image in their making of the selected cyber determinations.

Concise datasets include selected sensor data or derived data. Using video-formatted image sensor observations as an example, selected sensor data includes data from original sensor observation datasets. Informational representations from original sensor observation datasets are typically regarding the X and the Y line locations of each pixel on a sensor observation-derived representation's pixel grid and also the measured levels of red, green, or blue light at each pixel.

The derived data from concise datasets includes data that were derived from the processing of selected sensor data or selected derived data.

As an example, analyzing machines are configurable for utilizing one measure point in the locating of a pulse point on a sensor observation-derived representation of a specific person's face. A scalable configurable grid (explained later in this disclosure) is utilized for structuring a twenty-one pixel by twenty-one-pixel square with the single measure point at its center. The sums of the measurements of observed levels of red, green, or blue light from each column or from each row of pixels from within the scalable configurable grid are stored as derived data and the data can then be utilized by analyzing machines in their making of cyber determinations that heartbeats/pulses have occurred.

In addition, analyzing machines are configurable for utilizing the sums from one or more columns or rows from scalable configurable grids in their making of cyber determinations regarding a specific person's blood pressure.

Data from selected sensor data or derived data are stored in concise datasets for utilization in the making of selected cyber determinations. These cyber determinations can be made by analyzing machines in real time or at times thereafter. Analyzing machines are configurable for having no further use for original sensor observation datasets when the processing of all derived data has been completed and all selected sensor data or all derived data have been included in concise datasets. At this point in the operations of analyzing machines, original sensor observation datasets can be deleted or stored for later use.

Analyzing machines are configurable for comparing data from first series sensor observations of known analytically rich aspects, characteristics, or features of or from sensor observations or sensor observation subjects to data from second series sensor observations of yet-to-be-identified analytically rich aspects, characteristics, or features of or from second series sensor observations or sensor observation subjects.

For analyzing machines to accurately or reliably utilize informational representations from concise datasets in their making of selected cyber determinations, their processing of the first series observations and their processing of the second series observations of the same subject should result in their assignments of essentially the same standard informational representations to both sensor observations. Analyzing machines are configurable for utilizing the same standard tools, methodologies, or programming in the processing of second series observations as were used in the processing of the first series observations to which they will be compared.

Using working datasets that contain only two eyelid located measure points per image is an example of how analyzing machines can be configured to utilize: "a best performing blend of as simple, concise, and efficient as possible" as a strategy for all or parts of analyzing machines and their operations.

Analyzing machines, through their utilization of measure points or concise datasets, are configurable for accurately or reliably making selected cyber determinations from a complete spectrum of cyber determinations that can be made regarding or utilizing sensor observations or sensor observation subjects. Analyzing machines can be configured to do so utilizing combinations of tools, methodologies, or programming that enable the operations of analyzing machines to achieve the best performance while still remaining as simple, concise, and efficient as possible.

The present disclosure pertains to scalable, configurable, universal, complete spectrum, sensor data analyzing machines;

analyzing machines comprise analyzing machine resources that include: (a) computers, (b) tools, (c) methodologies, (d) programming, (e) information, (f) selected criteria, (g) data, and (h) other necessary resources;

analyzing machine resources are from a complete spectrum of resources that can be used as parts of analyzing machines or as parts of analyzing machine operations;

analyzing machines, or parts thereof, can be utilized for purposes from a complete spectrum of purposes for which analyzing machines or parts thereof can be utilized;

the computers include tangible, non-transient memory devices and input devices or output devices;

analyzing machines utilize all or parts of their analyzing machine resources for: (a) selecting or deriving data that is then included in concise datasets, or (b) utilizing data from concise datasets in their making of selected cyber determinations regarding or utilizing sensor observations or sensor observation subjects;

concise datasets are utilized by analyzing machines in their making of selected cyber determinations regarding or utilizing sensor observations or sensor observation subjects;

the concise datasets are utilizable for purposes from a complete spectrum of purposes for which concise datasets can be utilized;

the concise datasets include selected sensor data or derived data;

the selected sensor data includes informational representations that were selected from original sensor observation datasets;

derived data includes informational representations that were derived from the processing of (i) informational representation that were selected from original sensor observation datasets, or (ii) informational representations that were selected from derived data;

selected sensor data or derived data are utilizable by analyzing machines in their making of selected cyber determinations regarding or utilizing sensor observations or sensor observation subjects;

analyzing machines utilize selected tools, methodologies, or programming for their processing of derived data, these tools, methodologies, or programming are from a complete spectrum of tools, methodologies, or programming that can be utilized in the deriving of data for or from concise datasets;

analyzing machines are configurable for utilizing measure points in their locating of selected analytically rich aspects, characteristics, or features of or from sensor observation-derived representations of sensor observations or sensor observation subjects;

measure points are utilizable by analyzing machines in their making of selected cyber determinations regarding or utilizing sensor observations or sensor observation subjects;

analyzing machines assign appropriate informational representations to measure points and also to the analytically rich aspects, characteristics, or features of or from sensor observation-derived representations that are located through utilization of measure points;

the analytically rich aspects, characteristics, or features of or from sensor observations or sensor observation subjects are from a complete spectrum of analytically rich aspects, characteristics, or features of or from sensor observations or sensor observation subjects;

the analytically rich aspects, characteristics, or features of or from measure points are from a complete spectrum of analytically rich aspects, characteristics, or features of or from measure points;

the cyber determinations are from a complete spectrum of selected cyber determinations regarding or utilizing sensor observations, sensor observation subjects, or measure points;

the complete spectrum of cyber determinations regarding or utilizing sensor observations, sensor observation subjects, or measure points includes cyber determinations that identify tells that are utilizable by analyzing machines in their accurate or reliable making of selected cyber determinations regarding or utilizing sensor observations, sensor observation subjects, or measure points;

the tells are from a complete spectrum of sensor-observable tells regarding or utilizing sensor observations, sensor observation subjects, or measure points;

wherein the selected cyber determinations are utilizable for purposes from a complete spectrum of purposes for which cyber determinations regarding or utilizing sensor observations, sensor observation subjects, or measure points can be utilized;

analyzing machines are configurable for making selected cyber determinations in real time or at times thereafter;

analyzing machines are configurable for making at least one member selected from the group consisting of (a) one-time, single event cyber determinations regarding or utilizing sensor observations, sensor observation subjects, or measure points, (b) intermittently provided cyber determinations regarding or utilizing sensor observations, sensor observation subjects, or measure points, and (c) constantly provided cyber determinations regarding or utilizing sensor observations, sensor observation subjects, or measure points;

analyzing machines utilize information from a complete spectrum of information in their selecting, deriving, or processing of data for or from concise datasets or their making of selected cyber determinations;

the complete spectrum of information includes information from sensor observations;

sensor observations are made by sensors from a complete spectrum of sensors that can be utilized by analyzing machines in their making of cyber determinations regarding or utilizing sensor observations or sensor observation subjects;

analyzing machines are configurable and all or parts of their resource or their operations can be configured for utilization in one or more configurations;

analyzing machines are scalable, regarding included or utilized analyzing machine resources, to fall at a point in a range of from a minimum, to a maximum, wherein at the minimum analyzing machines are scaled to only include or utilize the resources that are needed in their making of the least complex selected cyber determinations, regarding included or utilized analyzing machine resources, and wherein at the maximum, analyzing machines are scaled to include or utilize all analyzing machine resources;

sensor observations or sensor observation subjects are from a complete spectrum of sensor observations or sensor observation subjects; and analyzing machines further comprise and utilize, in any sequence, at least one part of at least one operation selected from a group consisting of:

(a) first series observation operations, wherein analyzing machines are configured for utilizing first series sensor observations; wherein first series sensor observations or subjects of the first series sensor observations have previously determined analytically rich aspects, characteristics, or features; analyzing machines recognize the previously determined aspects, characteristics, or features; analyzing machines assign appropriate informational representations regarding the recognized aspects, characteristics, or features of or from the sensor observations or the sensor observation subjects; the assigned informational representations are utilizable by analyzing machines in their making of selected cyber determinations regarding or utilizing sensor observations or sensor observation subjects; analyzing machines include assigned informational representations of or from the first series observations in first series observation concise datasets, (b) second series observation operations, wherein analyzing machines are configured for utilizing second series sensor observations; wherein second series sensor observations or subjects of the second series observations have selected yet-to-be-determined analytically rich aspects, characteristics, or features; analyzing machines recognize yet-to-be-determined analytically rich aspects, characteristics, or features; analyzing machines assign appropriate informational representations regarding the yet-to-be-determined analytically rich aspects, characteristics, or features of or from the sensor observations or the sensor observation subjects; the assigned informational representations are utilizable by analyzing machines in their making of selected cyber determinations regarding or utilizing sensor observations or sensor observation subjects; analyzing machines include assigned informational representations of or from the second series observations in second series observation concise datasets, (c) measure point operations, wherein analyzing machines utilize measure points in their locating of selected analytically rich aspects, characteristics, or features of or from sensor observation-derived representations of sensor observations or sensor observation subjects; wherein analyzing machines assign appropriate informational representations regarding the measure points or the selected analytically rich aspects, characteristics, or features; wherein the informational representations are stored or utilized in the making of selected cyber determinations regarding or utilizing sensor observations or sensor observation subjects, (d) concise datasets operations, wherein analyzing machines select, derive, or utilize data for or from concise datasets; wherein the concise datasets include selected sensor data or derived data; wherein the selected sensor data includes informational representations from original sensor observation datasets, and wherein the derived data is comprised of informational representations that were derived from (i) the processing of selected informational representation from original sensor observation datasets, or (ii) the processing of selected informational representations from derived data; wherein informational representations from the selected data or the derived data are utilizable by analyzing machines in their making of selected cyber determinations regarding or utilizing sensor observations or sensor observation subjects, (e) matching operations, wherein analyzing machines match selected informational representations from second series observation concise datasets to selected comparable informational representations from first series observation concise datasets, (f) comparing operations, wherein analyzing machines make comparisons of selected informational representations from second series observation concise datasets to selected informational representations from first series observation concise datasets; wherein the analyzing machines utilize the comparisons (i) for providing conclusions, or (ii) in their making of selected cyber determinations, (g) determining operations, wherein analyzing machines utilize conclusions from comparing operations or information in their making of selected cyber determinations regarding or utilizing sensor observations or sensor observation subjects, and (h) reporting operations, wherein analyzing machines make selected reports regarding or utilizing aspects, characteristics, or features of or from their operations.

Analyzing machines are further configurable for utilizing: (a) tools, (b) methodologies, (c) programming, (d) people, or (d) combinations thereof in their selecting of aspects, characteristics, or features of or for operations of analyzing machines, wherein the tools, methodologies, and programming are selected from a complete spectrum of tools, methodologies, and programming that can be utilized in the selecting of aspects, characteristics, or features of or for operations of analyzing machines.

Analyzing machines are further configurable for utilizing at least one member selected from the group consisting of (a) tools, (b) methodologies, (c) programming, (d) data, (e) information, (f) people, or (g) combinations thereof, in their making of selected determinations regarding points where selected measure points will be located on sensor observation-derived representations, and wherein at least one member selected from the group consisting of (i) tools, (ii) methodologies, (iii) programming, (iv) data, (v) information, (vi) people, or (vii) combinations thereof are utilizable in the making of types of determinations selected from the group consisting of:

(1) determinations of points where selected measure points will be located on sensor observation-derived representations of only one specific sensor observation subject, (2) determinations of points where selected measure points will be located on sensor observation-derived representations of sensor observation subjects that are members of specific groups of sensor observations subjects, and (3) determinations of points where selected measure points will be located on sensor observation-derived representations of sensor observation subjects that are from a complete spectrum of sensor observation subjects.

In some embodiments of analyzing machines, a complete spectrum of subjects of sensor observations includes people as sensor observation subjects;

wherein analytically rich aspects, characteristics, or features of the people include aspects, characteristics, or feature from a complete spectrum of analytically rich aspects, characteristics, or features of people;

wherein measure points are utilizable by analyzing machines in their locating of selected analytically rich aspects, characteristics, or features of or from sensor observation-derived representations of people;

wherein the measure points are utilizable for purposes from a complete spectrum of purposes for that measure points that are used in the locating of selected analytically rich aspects, characteristics, or features of or from sensor observation-derived representations of people can be utilized;

wherein the spectrum of analytically rich aspects, characteristics, or features of or from sensor observation-derived representations of people includes: (a) scars, (b) marks, (c) tattoos, (d) fingerprint features, (e) axis points at joints, (f) tips of noses, (g) corners of eyes, (h) centers of pupils, (i) corners of mouths, (j) tips of fingers, (k) patterns of sweat glands, (l) coughs, (m) tremors, (n) shivers, (o) voices, or (p) any other analytically rich aspects, characteristics, or features of or from sensor observation-derived representations of people.

Analyzing machines are further configurable for the making of selected cyber determinations regarding or utilizing sensor observations or sensor observation subjects, wherein the sensor observations are made: (a) at points in time, or (b) over periods of time, and the analyzing machines include, in concise datasets, informational representations regarding or utilizing selected analytically rich changes that occur over time to sensor-observable aspects, characteristics, or features of or from sensor observation-derived representations of sensor observations or sensor observation subjects.

Analyzing machines are further configurable for utilizing analytically rich changes that occur to people over time; the analytically rich changes include changes that occur to sensor observation-derived representations of people from a group consisting of sensor-observable analytically rich changes that occur over time to sensor observation-derived representations of aspects, characteristics, or features of a peoples': (a) heads, (b) faces, (c) mouths, (d) eyes, (e) eyebrows, (f) noses, (g) arms, (h) hands, (i) fingers, (j) legs, (k) feet, (l) necks, (m) torsos, (n) skin, (o) hearts, (p) stomachs, (q) intestines, (r) livers, (s) kidneys, (t) lungs, (u) breath, (v) vascular systems, (w) brains, (x) spinal cords, (y) neural systems, (z) neural activity, (aa) skeletons, (bb) blood, (cc) odors, (dd) voices, (ee) movement, (ff) tips of noses, (gg) corners of eyes, (hh) centers of pupils, (ii) axis points at joints, or (jj) aspects, characteristics, or features of people from a complete spectrum of other aspects, characteristics, or features of sensor observation-derived representations of people where sensor-observable analytically rich changes occur over time.

Analyzing machines are further configurable for making cyber determinations regarding any indicated measure of probability that exists of one specific yet-to-be-identified person being the same person as one specific known person, wherein these cyber determinations range from the making of cyber determinations that one specific yet-to-be-identified person absolutely is not one specific known person, through the making of cyber determinations of any intermediate indicated measure of probability that exists of one specific yet-to-be-identified person being one specific known person, to the making of cyber determinations that one specific yet-to-be-identified person absolutely is one specific known person.

Analyzing machines are further configurable for making selected cyber determinations that are utilized in processes of accurately or reliably granting or denying people or cyber devices access to at least one member selected from the group consisting of: (a) all or parts of analyzing machines, (b) all or parts of resources that are being utilized by analyzing machines, or (c) all or parts of resources that are utilizing analyzing machines.

Analyzing machines are further configurable for being utilized in the accurate or reliable cyber testing of the identities of specific people; wherein these cyber identity tests can be configured to utilize selected levels of identity testing participation by people who are subjects of these cyber identity tests; and wherein the selected levels of participation range from tested people being observable by sensors, but not consciously engaged in the cyber identity testing, to the tested people being observable and consciously engaged participants in the cyber identity testing.

Analyzing machines are further configurable for cyber identity testing to include repeating operations; wherein parts of first series observations of one specific known person are selected to be repeated by one specific yet-to-be-identified person; wherein the one specific yet-to-be-identified person performs selected repetitions; wherein analyzing machines assign appropriate informational representations regarding, or utilizing at least one member selected from the group consisting of: (a) the observations, (b) the repetitions, and (c) analytically rich aspects, characteristics or features of or from the yet-to-be-identified person while the yet-to-be-identified person is performing the repetitions; wherein the second series observation concise datasets of the repetitions include informational representations that were appropriately assigned to the repetitions by analyzing machines; and wherein the second series observation concise datasets from the repetitions are utilizable by analyzing machines in their making of cyber determinations regarding the identities of yet-to-be-identified people.

Analyzing machines are configurable for being utilized, in whole or in part, as universal health metrics monitors, wherein universal health metrics monitors are configured for monitoring or recording selected parts of sensor observations of selected analytically rich aspects, characteristics, or features of peoples' health;

universal health metrics monitors are configurable for making or reporting on selected cyber determinations regarding or utilizing selected sensor-observed analytically rich aspects, characteristics, or features of peoples' health;

universal health metrics monitors are configurable for making cyber determinations from a complete spectrum of cyber determinations that can be made regarding or utilizing health-related analytically rich aspects, characteristics, or features of or from sensor observation-derived-representations of people;

the complete spectrum of cyber determinations regarding or utilizing health-related analytically rich aspects, characteristics, or features of or from sensor observation derived-representations of people includes cyber determinations that identify health-related tells regarding or utilizing analytically rich aspects, characteristics, or features of or from sensor observation-derived representations of people, wherein the health-related tells can be utilized by analyzing machines in their accurate or reliable making of cyber determinations that specific people have, had, or will have selected health-related occurrences that the people may, should, or do want to utilize or be made aware of;

wherein the health-related tells are from a complete spectrum of sensor-observable tells regarding or utilizing peoples' health;

wherein health-related tells are utilizable by universal health metrics monitors in their making of selected cyber determinations regarding or utilizing selected sensor-observed analytically rich aspects, characteristics, or features of peoples' health;

wherein the selected cyber determinations are utilizable by universal health metrics monitors in their monitoring of, or their reporting on, selected sensor-observed analytically rich aspects, characteristics, or features of or from a peoples' health;

wherein monitoring operations of, or recording operations of, universal health metrics monitors can be made: (a) as one-time, single events, (b) intermittently, or (c) constantly;

wherein reporting operations of universal health metrics monitors are configurable for the making of reports from a complete spectrum of reports that can be made regarding or utilizing health-related analytically rich aspects, characteristics, or features of or from sensor-observation-derived representations of people;

wherein recordings are made of all or parts of selected sensor observations;

wherein people or universal health metrics monitors select all or the parts of selected sensor observations that are to be recorded;

wherein universal health metrics monitors are configurable for including, in concise datasets, all or selected parts of sensor observation datasets;

wherein the sensor observations are made at points in time or over periods of time;

wherein the any other necessary resources can include sensors that are utilizable by universal health metrics monitors in their recording of selected sensor observations of selected analytically rich aspects, characteristics, or features of peoples' health;

wherein the sensors are selected from a complete spectrum of sensors that can be utilized in the recording of analytically rich health-related observations of people; and wherein the complete spectrum of sensors includes: (i) internal sensors, (ii) external sensors, (iii) wearable sensors, (iv) sensors that are in an observable proximity of people who are subjects of sensor observations, or (v) other sensors that are utilizable in the making of selected cyber determinations regarding or utilizing peoples' health.

Universal health metrics monitors are further configurable for being utilized in the making of selected one-time, single event, health-related cyber test determinations regarding or utilizing selected sensor-observed analytically rich aspects, characteristics, or features of peoples' health;

wherein selected one-time, single event, health-related cyber test determinations can be made or utilized in real time or at times thereafter;

wherein selected one-time, single event, health-related cyber test determinations are made utilizing data from a complete spectrum of sensors that can be utilized in the making of one-time, single event, health-related cyber test determinations regarding or utilizing selected sensor-observable analytically rich aspects, characteristics, or features of peoples' health;

wherein the selected analytically rich aspects, characteristics, or features of the health of tested people are from a complete spectrum of sensor-observable analytically rich aspects, characteristics, or features of peoples' health;

wherein the complete spectrum of health-related cyber test determinations regarding or utilizing selected sensor-observable analytically rich aspects, characteristics, or features of peoples' health includes test determinations regarding the presence of: (a) COVID-19, (b) H1N1, (c) Ebola, (d) cancer, or (e) a complete spectrum of other selected aspects, characteristics, or features of peoples' health that can be sensor-observed, tested, and accurately or reliably reported on;

wherein the one-time, single event, health-related cyber test determinations regarding or utilizing selected sensor-observed analytically rich aspects, characteristics, or features of peoples' health can be utilized for purposes from a complete spectrum of purposes for which one-time, single event, health-related cyber test determinations regarding or utilizing sensor-observed analytically rich aspects, characteristics, or features of peoples' health can be utilized;

wherein the complete spectrum of purposes for which one-time, single event, health-related cyber test determinations regarding or utilizing sensor-observed analytically rich aspects, characteristics, or features of peoples' health can be utilized includes the making of health-related cyber test determinations regarding or utilizing sensor-observed analytically rich aspects, characteristics, or features of peoples' health prior to or immediately prior to the tested people being granted or denied access to at least one member selected from the group consisting of: (i) schools, (ii) public transportation, (iii) houses of worship, (iv) workplaces, (v) events, (vi) sporting activities, (vii) restaurants, (viii) bars, (ix) stores, (x) hospitals, (xi) parks, (xii) prisons, (xiii) nursing homes, (xiv) grocery stores, (xv) theaters, (xvi) gyms, (xvii) health care providers' offices, (xviii) concerts, (xix) salons, (xx) meat processing plants, or (u) other places or activities where it is required or desired to determine if tested people do or do not have selected health-related aspects, characteristics, or features that would or should exclude specific tested people from gaining initial access to, or from having continued access to places or activities.

Analyzing machines are further configurable for utilizing measure points in their locating of sensor observation-derived representations of selected analytically rich aspects, characteristics, or features of or from sensor observation-derived representations of the faces of people;

wherein the measure points are utilized for purposes from a complete spectrum of purposes for which measure points that are utilized in the locating of analytically rich aspects, characteristics or features of or from sensor observation-derived representations of the faces of people can be utilized;

wherein the complete spectrum of purposes for which measure points that are used in the locating of selected analytically rich aspects, characteristics, or features of or from sensor observation-derived representations of the faces of people can be utilized includes utilizing measure points in the processes of: (a) determining the identities of yet-to-be-identified people, (b) authenticating the claimed identities of yet-to-be-identified people, (c) determining peoples' facial affects, (d) determining peoples' facial expressions, (e) determining the gaze of peoples' eyes, (f) determining sensor, or camera angles, (g) determining sensor observation lighting circumstances, (h) determining peoples' poses, (i) determining what portions of peoples' faces are being observed, (j) determining measures of peoples' state of mental, or physical health, (k) determining peoples' pulse rates, (l) determining peoples' blood pressure, (m) determining relationships between sensors and measure points that are located on sensor observation-derived representations of peoples' faces, or (n) making determinations from a complete spectrum of other determinations for which measure points that are used in the locating of selected analytically rich aspects, characteristics, or features of, or from sensor observation-derived representations of peoples' faces can be utilized.

Analyzing machines are configurable for the making of selected cyber determinations regarding or utilizing measured locations of, or measured orientations of, selected analytically rich aspects, characteristics, or features of or from sensor observation-derived representations of people;

wherein the sensor observation-derived representation of the analytically rich aspects, characteristics, or features of or from people are from a complete spectrum of sensor observation-derived representations of analytically rich aspects, characteristics or features of or from people;

wherein measured locations of, or measured orientations of selected analytically rich aspects, characteristics, or features of or from sensor observation-derived representations of people include, for example, measured locations of, or measured orientations of: (a) sensor observation-derived representations of fingerprint features on sensor observation-derived representation of peoples' fingers or fingerprints, (b) sensor observation-derived representations of tattoos on sensor observation-derived representations of people, (c) sensor observation-derived representations of scars on sensor observation-derived representations of people, (d) sensor observation-derived representations of marks on sensor observation-derived representations of people, (e) sensor observation-derived representations of patterns of sweat glands on sensor observation-derived representations of people, (f) sensor observation-derived representations of pulse points on sensor observation-derived representations of people, or (g) sensor observation-derived representations of analytically rich aspects, characteristics, or features of people from a complete spectrum of other sensor observation-derived representations of analytically rich aspects, characteristics, or features of people.

Analyzing machines are configurable for utilizing measure points in their locating of sensor observation-derived representations of the tips of peoples' fingers;

wherein the measure points are used for purposes from a complete spectrum of purposes for which measure points that are utilized in the locating of sensor observation-derived representations of peoples' fingertips can be used;

wherein the complete spectrum of purposes includes utilization of the measure points as components of fingertip-to-cyber device touchless user interfaces; and wherein the cyber devices are types of cyber devices from a complete spectrum of types of cyber devices that can utilize fingertip-to-cyber device touchless user interfaces.

Analyzing machines are configurable for utilizing measure points in their locating of selected analytically rich aspects, characteristics, or features from sensor observation-derived representations of people, wherein the measure points can be utilized as components of human-to-cyber device touchless user interfaces;

wherein the human-to-cyber device touchless user interfaces, using the measure points, are utilized for purposes from a complete spectrum of purposes for which human-to-cyber device touchless user interfaces can be utilized; and wherein the cyber devices are types of cyber devices from a complete spectrum of types of cyber devices that can utilize human-to-cyber device touchless user interfaces.

Analyzing machines are configurable for utilizing measure points in their locating of axis points from sensor observation-derived representations of joints of people;

wherein measure points that locate axis points are utilized for purposes from a complete spectrum of purposes for which measure points that locate sensor observation-derived representations of axis points of peoples' joints can be utilized; and wherein the complete spectrum of purposes for which measure points that are utilized in the locating of sensor observation-derived representations of axis points of joints of people includes: (a) making selected cyber determinations regarding or utilizing observed geometries at sensor observation-derived representation of joints of people, or (b) making selected cyber determinations that utilize measure points that locate sensor observation-derived representations of axis points of joints of people for purposes from a complete spectrum of other purposes for which measure points that locate sensor observation-derived representations of axis points of joints of people can be utilized.

Analyzing machines are configurable for being utilized in the making of selected cyber determinations regarding or utilizing analytically rich aspects, characteristics, or features of observed geometries of sensor observation-derived representation of joints of people; and wherein selected analytically rich aspects, characteristics, or features of observed geometries of sensor observation-derived representations of joints of people can be utilized for purposes from a complete spectrum of purposes for which analytically rich aspects, characteristics, or features of observed geometries of sensor observation-derived representations of joints of people can be utilized.

Analyzing machines are configurable for utilizing selected measure points in their making of selected measurements;

wherein measurements that are made through utilization of measure points are from a complete spectrum of measurements that can be made through use of measure points that are utilized in locating selected analytically rich aspects, characteristics, or features of or from sensor observation-derived representations; and wherein the complete spectrum of measurements that can be made through utilization of measures point includes: (a) measured distances between measure points, (b) measured angles where lines between measure points meet or intersect, (c) measured locations of measure points, aspects, characteristics, or features, (d) measured orientations of measure points, aspects, characteristics, or features, (e) measured relationships between measure points, aspects, characteristics, or features, (f) time of capture of sensor observations or parts thereof, (g) measured pressures at or in the areas of measure points, (h) measured temperatures at or in the areas of measure points, (i) measured levels of colored light at or in the areas of measure points, (j) measured grey scale levels at or in the areas of measure points, (k) measured odors at or in the areas of measure points, (l) measured presences at or in the areas of measure points, (m) measured sound at or in the areas of measure points, (n) measured energy at or in the areas of measure points, (o) measured presence of chemicals at or in the areas of measure points, or (p) measures of sensor-observable analytically rich aspects, characteristics, or features from a complete spectrum of other measurable sensor-observable analytically rich aspects, characteristics, or features of or from sensor observation-derived representations that can be located through the utilization of measure points.

Analyzing machines are configurable for performing analyzing machine operations, or parts thereof, in any usable order, or sequence.

Analyzing machines are configurable for achieving selected attainable level of accuracy goals for selected cyber determinations, and the attainable level of accuracy goals falls in a range extending from 0% accuracy, and goes up to, and includes, 100% accuracy.

Analyzing machines are configurable for utilizing information or informational representations from sources that are not first series observations or second series observations.

Analyzing machines are configurable for manipulating, in possible ways, operations of analyzing machine utilized resources, or operations of analyzing machines; wherein the manipulation provides analyzing machines with selections of possible utilizations; wherein the manipulation is utilized for purposes from a complete spectrum of purposes for which manipulating can be utilized; wherein the complete spectrum of purposes for manipulating includes aiding in the making of selected cyber determinations.

Analyzing machines are configurable for utilizing all or part of sensor observation datasets from sources that are not first series observation operations as all or part of first series observation concise datasets, and analyzing machines are configurable for utilizing all or part of sensor observation datasets from sources other than second series observation operations as all or part of second series observation concise datasets.

Analyzing machines are configurable for including analyzing machine history; wherein analyzing machine history is comprised of analyzing machine history records; wherein analyzing machine history records can be used for purposes from a complete spectrum of purposes for which analyzing machine history records can be used.

The present disclosure further pertains to sensor data analyzing machines that comprise computing devices, sensor data, tools, methodologies, and programming that are used for capturing, selecting, deriving, or utilizing data for or from concise datasets; wherein data for or from concise datasets are utilizable by analyzing machines in their making of selected cyber determinations regarding or utilizing sensor observations or sensor observation subjects; the analyzing machines further comprise deriving or utilizing information, from points in time or from periods of time, from a complete spectrum of information that includes information regarding observed analytically rich aspects, characteristics, or features of or from sensor observations or subjects of sensor observations, thereby obtaining sensor observation-derived information;

wherein the sensor observations are types of sensor observation from a group consisting of (a) visual sensor observations, (b) audible sensor observations, (c) thermal sensor observations, (d) olfactory sensor observations, (e) tactile sensor observations, (f) chemical sensor observations, or (g) types of sensor observations from a complete spectrum of other types of sensor observations that can be utilized by analyzing machines;

wherein analyzing machines capture, select, derive, or utilize data for or from concise datasets, or make selected cyber determinations through utilization of (i) computing devices, (ii) sensor data, (iii) necessary programming, (iv) information, (v) criteria that are utilized by analyzing machines, and (vi) other necessary resources;

wherein analyzing machines make at least one type of cyber determination selected from the group consisting of (1) one-time, single event cyber determinations, (2) intermittently made cyber determinations, and (3) constantly made cyber determinations;

wherein selected cyber determinations are utilized for purposes from a complete spectrum of purposes for which cyber determinations regarding or utilizing sensor observations or sensor observation subjects can be utilized; and wherein analyzing machines further comprise utilizing at least one part of at least one operation selected from a group consisting of (a) first series observation operations, wherein analyzing machines utilize sensor observations; wherein sensor observations or subjects of the sensor observations have previously determined aspects, characteristics, or features; analyzing machines recognize the aspects, characteristics, or features; wherein recognized aspects, characteristics, or features are utilizable by analyzing machines in their making of selected cyber determinations; analyzing machines assign appropriate informational representations regarding selected known aspects, characteristics, or features of sensor observations or sensor observation subjects; analyzing machines include all or parts of the informational representations in first series observation concise datasets, (b) second series observation operations, wherein analyzing machines utilize sensor observations; and wherein sensor observations or subjects of the sensor observations have selected yet-to-be-determined aspects, characteristics, or features; analyzing machines recognize selected yet-to-be-determined aspects, characteristics, or features; analyzing machines assign appropriate informational representations regarding selected yet-to-be-determined aspects, characteristics, or features of sensor observations or sensor observation subjects; wherein analyzing machines include all or part of the informational representations in second series observation concise datasets, (c) measure point operations, wherein analyzing machines utilize measure points in their locating of selected analytically rich aspects, characteristics, or features of, or from sensor observation-derived representations of sensor observations, or sensor observation subjects; wherein analyzing machines assign appropriate informational representations regarding the measure points, aspects, characteristics, or features of or from the sensor observation-derived representations; wherein all or part of the informational representations are stored or utilized by analyzing machines in their making of selected cyber determinations regarding or utilizing the sensor observations or the sensor observation subjects, (d) concise datasets operations, wherein analyzing machines utilize concise datasets in their making of selected cyber determinations; the concise datasets include selected sensor data or derived data; wherein the selected sensor data comprises informational representation that were selected from original sensor observation datasets, and wherein the derived data comprises informational representation that were derived from (i) the processing of selected informational representations from original sensor observation datasets, or (ii) the processing of selected informational representations from derived data; wherein the informational representations from the selected sensor data or the informational representations from the derived data are utilizable by analyzing machines in their making of selected cyber determinations regarding, or utilizing sensor observations, or sensor observation subjects; and wherein the selected derived data are derived utilizing tools, methodologies, or programming from a complete spectrum of tools, methodologies, or programming that can be utilized in the deriving of informational representations from sensor data or from or for derived data, (e) matching operations, wherein analyzing machine matching operations include matching informational representation from second series observation concise datasets to comparable informational representation from first series observation concise datasets, (f) comparing operations, wherein analyzing machine comparing operations include comparing of informational representation from second series observation concise datasets to comparable informational representation from first series observation concise datasets, and providing conclusions or determinations from the comparing, (g) determining operations, wherein analyzing machines utilize conclusions or determinations from comparing operations or information in their making of selected cyber determinations, and (h) reporting operations, wherein analyzing machines include reporting operations, wherein analyzing machines make selected reports regarding or utilizing selected aspects, characteristics, or features of all or parts of cycles of utilization of the analyzing machines.

BRIEF DESCRIPTION OF THE DRAWING

FIG. 1 is an illustration of a particular non-limiting embodiment of operations of a sensor data analyzing machine, and its associated analyzing machine resources in accordance with the teachings herein.

DETAILED DESCRIPTION

The present disclosure pertains to scalable, configurable, universal, complete spectrum, sensor data analyzing machines that are configurable for making selected cyber determinations regarding or utilizing sensor observations or sensor observation subjects. Analyzing machine resources include computing devices, tools, methodologies, programming, data, information, selected criteria, and other necessary resources that are utilized by the analyzing machines in their making of selected cyber determinations regarding or utilizing sensor observations or sensor observation subjects. The selected cyber determinations are from a complete spectrum of cyber determinations that can be made regarding or utilizing sensor observations or sensor observation subjects.

Analyzing machines are configurable for making selected cyber determinations regarding or utilizing measure points. These cyber determinations are used in the locating of selected analytically rich aspects, characteristics, or features of or from sensor observation-derived representations.

Analyzing machines are configurable for assigning or utilizing informational representations regarding or utilizing measure points or analytically rich aspects, characteristics, or features of or from sensor observation-derived representations.

Additionally, analyzing machines are configurable for utilizing concise datasets in their making of selected cyber determinations.

Unless otherwise specified herein, each of the following will apply throughout this entire disclosure:

(a) analyzing machines are scalable and therefore they can be scaled to include analyzing machine resources from any point in a range of included or utilized analyzing machine resources, wherein at one end of the range analyzing machines are scaled to include or utilize the fewest analyzing machine resources, and at the other end of the range analyzing machines are scaled to include or utilize all analyzing machine resources;

(b) analyzing machines are configurable and they can be configured to be utilized in one or more configurations;

(c) analyzing machines or parts thereof are configurable for universal utilization;

(d) analyzing machines are configurable for providing selections of criteria, wherein criteria are selected from a complete spectrum of criteria that are utilizable by analyzing machines in their making of selected cyber determinations regarding or utilizing sensor observations or sensor observation subjects;

(e) analyzing machines are complete spectrum analyzing machines and they are configurable for utilizing analyzing machine resources from a complete spectrum of analyzing machine resources that are utilizable by the analyzing machines in their making of selected cyber determinations regarding or utilizing sensor observations or sensor observation subjects from a complete spectrum of sensor observations or sensor observation subjects. Further, analyzing machines are configurable for providing for cyber determination needs from a complete spectrum of needs for cyber determinations regarding or utilizing sensor observations or sensor observation subjects; and (f) an operational goal of analyzing machines is to preferably utilize best performing blends of as simple, concise, and efficient operations as possible.

The present disclosure primarily addresses the use of video-formatted image sensor observations of people, however analyzing machines are configurable for making selected cyber determinations regarding or utilizing sensor observations or sensor observation subjects from a complete spectrum of sensor observations or sensor observation subjects.

Definitions

In the present disclosure, the following terms or phrases have the meanings indicated below.

Absolutely unique: occurring at a ratio of one to the total (non-zero) number of first series observation datasets. Thus, for example, if there are 100 first series observation datasets, then an occurrence is absolutely unique if it occurs at a ratio of 1:100.

Adjusting factors: tools, methodologies, programming, or combinations thereof that are utilized to enable analyzing machines to accurately or reliably make selected cyber determinations when there are observation circumstances or analytically rich aspects, characteristics, or features of or from second series observations or second series observation subjects that are not exact matches to the observation circumstances or analytically rich aspects, characteristics, or features of or from the first series observations or the first series observation subjects to which they are being matched or compared.

Analytically rich: being usable by analyzing machines in their accurate or reliable making of selected cyber determinations.

Analyzing machines: one or more scalable, configurable, universal, complete spectrum sensor data analyzing machines.

Artificial intelligence/AI: the use of cyber resources that include computing devices, tools, methodologies, programming, or necessary data, in the answering of selected questions, and then utilizing those answers to determine the requested resources to deliver.

Aspects: one or more aspects, characteristics, or features of or from sensor observation-derived representations of sensor observations or sensor observation subjects.

Aspects, characteristics, or features: at least one member selected from the group consisting of: (a) aspects, (b) characteristics, or (c) features of or from sensor observation-derived representations of sensor observations or sensor observation subjects.

Behavioral analysis: analysis of sensor-observed behavior of organisms or devices.

Biological characteristics: biological aspects, characteristics, or features of biological organisms, including people, that are sensor observable.

Cameras: image sensors; video-formatted image sensors.

Capture/capturing: the use of cyber resources for acquiring and recording cyber sensor observations.

Characteristics: one, or more aspects, characteristics, or features of or from sensor observation-derived representations of sensor observations, or sensor observation subjects.

Complete spectrum: the complete set of possible choices for a given variable or option, which includes the subset of available choices for any given variable or option; thus, for example, the complete spectrum of cyber resources is the complete set of possible cyber resources, which includes all available cyber resources.

Concise: including or utilizing little or no unnecessary data, analyzing machine resources, or parts thereof in the making of selected cyber determinations.

Concise datasets: small datasets; datasets that contain little or no unnecessary data; datasets that are typically at least 90% smaller than the original sensor observation datasets from which they were selected or derived; datasets that are comprised of selected analytically rich sensor observation data or analytically rich derived data.

Constant determinations: cyber determinations that are made at any frequency that essentially results in the uninterrupted continuous making of the cyber determinations.

Criteria: a group of selectable options that contains one or more members.

Cyber: utilizing non-biological processing of programming, the term includes anything (such as, for example, devices, tools, methodologies, programming, or files) that utilizes, or are utilized for, non-biological processing of programming.

Cyber determinations: one, or more questions that are answered through utilization of cyber resources.

Cyber portals: cyber devices that are configured to perform at least one action selected from the group consisting of: (a) sending cyber interactions from people who are using cyber portals, (b) receiving cyber interactions, (c) providing sensor observations of people who are using cyber portals for use in determining the identities of those people, (d) providing output that enables cyber portal users to perceive cyber interactions, (e) enabling people to interact with cyber devices, (f) enabling people to interact with cyber interactions, and (g) utilization for purposes from a complete spectrum of other purposes for which cyber portals can be utilized.

Cyber resources: one or more cyber assets; one or more cyber resources.

Digitation: at least one fingertip that is observed by sensors and touchlessly used by a person to communicate the person's intent to interact with cyber resources.

Derived data: data that are derived from the processing of selected sensor data or selected derived data.

Determinations: determinations or cyber determinations.

Determinations of identity: cyber determinations of previously unknown identity or cyber determinations for authenticating or verifying claimed identity.

Enrolling/enrollment: the initial collecting or processing of sensor observations of one specific enrollee, wherein the processing results in the assignment of appropriate informational representations that make up the initial first series observation concise datasets (the cyber identity or identifiers) for the one specific enrollee; informational representations from enrollment can be utilized as all or part of the first series observation concise datasets of the one specific observation subject that is the enrollee.

Features: one or more aspects, characteristics, or features of or from sensor observation-derived representations of sensor observations or sensor observation subjects.

Final cyber determinations: the last cyber determinations in one or more series of cyber determinations.

Fingers: one or more fingers or thumbs.

Frames: single images that are parts of sequential streams of video-formatted images.

From: from; selected from.

Identity determinations: cyber determinations regarding identity.

In areas of: in the areas of.

Indicators: analytically rich aspects, characteristics, or features of or from sensor observation-derived representations that are assigned appropriate informational representations that are stored for utilization in the making of selected cyber determinations.

Informational representations: data; designations, names, labels, or measurements that are appropriately assigned to sensor-observed analytically rich aspects, characteristics, or features of or from sensor observation-derived representations of sensor observations or sensor observation subjects.

Initial cyber determinations: the first question to be answered in a series of questions to be answered through the use of cyber resources.

Intermediate cyber determination: cyber determinations that are utilized in the answering of selected questions that are not exclusively initial cyber determinations or final cyber determinations from a series of cyber determinations.

Known person: a person who is the known subject of one or more first series observation concise datasets.

Machine learning: the use of cyber resources for the making of one or more cyber determination, wherein the one or more cyber determination is then utilized to improve upon or further refine the results of one or more subsequent cyber determination.

Machines: machines; sensor data analyzing machines.

Measure points: points or pointers that are utilized in the locating of selected analytically rich aspects, characteristics, or features of or from sensor observation-derived representations; measure points are utilized to provide reproducible structures from which: (a) measurements are made, (b) structured analysis is performed on sensor observation-derived representations of sensor observations or sensor observation subjects, or (c) sensor observation-derived representations from multiple sensors or from multiple times of capture can reliably be aligned.

Multitudes: quantities of 100 or more.

Observation/observations: one or more sensor observations.

One time/one-time: occurring at only one specific point in time or occurring over only one specific short period of time.

Points: the smallest addressable locations from sensor observation-derived representations.

Physical analysis: analysis of sensor-observable physical aspects, characteristics, or features of sensor observation subjects.

Physiological analysis: analysis of sensor-observable physiological aspects, characteristics, or features of sensor observation subjects.

Prior art: prior art analyzing machines, analyzing machine tools, analyzing machine methodologies, or analyzing machine programming.

Real time/real-time: occurring at essentially the exact moment in time that a sensor observation is captured;

occurring at a time that was so close to the time when a sensor observation was captured that people would not notice latency.

Recognized: analytically rich aspects, characteristics, or features of or from sensor observation-derived representations that are accurately or reliably identified.

Selected determinations: selected cyber determinations regarding or utilizing sensor observations or sensor observation subjects.

Series: groups of one or more.

Smudges: sensor observed artifacts of prior light that were fully present at previous points in time; artifacts of prior light that are recognizable parts of sensor observation-derived representations; prior light from previous points in time (possibly in increments of 500 points in time or more per second) that can still be captured by sensors for one or more points in time past the final point in time when the sensor observed-representation of the fully present light was captured; artifacts of light that can be utilized in making selected cyber determinations regarding or utilizing what occurred at one or more points in time prior to when images were captured or recorded; artifacts of light that can be utilized in the making of selected cyber predictions of what might be observed in the future; reflected or refracted light that alters the observed levels of colored light at pixels that adjoin or that are in the areas of the refracted or the reflected light.

Smudge analysis: analysis of smudges from sensor observation-derived representations.

Spectrum: a complete spectrum; a complete set of possible choices for a given variable or option.

Tells: analytically rich aspects, characteristics, or features of or from sensor observation-derived representations that are utilizable by analyzing machines in their accurate or reliable making of one or more selected cyber determinations.

Unique: occurring at a selected ratio other than the ratio of absolutely unique.

Unique biological aspects, characteristics, or features: any single observable aspect, characteristic, or feature of a biological organism, or any combination of sensor observable aspects, characteristics, or features of one biological organism (e.g., a biological fingerprint) that are considered to be unique or absolutely unique to the one specific observed biological organism.

Video cameras: video-formatted image sensors.

Visual analysis: the analysis of images from image sensor observation-derived representations.

Y: designation for vertical lines from pixel grids.

Yet-to-be-identified person: one specific person who is a subject of a second series observation; one specific person who has not yet been determined to be the same person as one specific known person.

X: designation for horizontal lines from pixel grids.

Prior Art's Problems

Prior art's inability to fulfill the world's needs for accurate, or reliable real-time cyber determinations regarding or utilizing sensor observations or sensor observation subjects is due, in part, to the numerous limitations and inefficiencies of prior art and the tools, methodologies, and programming it utilizes.

Prior art utilizes tools, methodologies, and programming for its making of selected cyber determinations regarding or utilizing sensor observations or sensor observation subjects that have many, if not all, of the following problems or inefficiencies:

a. prior art requires a great deal of analysis or comparison in its making of initial, intermediate, or final cyber determination;

b. datasets from prior art can only be utilized in the making of one selected final cyber determination during each cycle of prior art's processing operations;

c. datasets from prior art are large and therefore inefficient to store, manage, or compare;

d. datasets from prior art are not interoperable and therefore the datasets from one prior art cannot be universally used with any or all other prior art;

e. prior art must reprocess second series observation datasets each time they are compared to different first series observation datasets;

f. prior art is not universally usable across a complete spectrum of sensor observation circumstances, wherein sensor observation circumstances include: lighting, pose, sensors utilized, positions of subjects relative to sensors, movements of sensors or sensor observation subjects, temperature, wind conditions, items on or around sensor observation subjects, other subjects of sensor observations, locations, or any other sensor observation circumstances from a complete spectrum of sensor observation circumstances;

g. prior art does not utilize all of the analytically rich aspects, characteristics, or features from sensor observations that are needed for achieving the highest attainable levels of accuracy in its making of selected cyber determinations regarding or utilizing sensor observations or sensor observation subjects;

h. prior art cannot utilize a complete spectrum of types of sensor observations or a complete spectrum of sensor-observable analytically rich aspects, characteristics, or features of or from sensor observations or sensor observation subjects;

i. prior art is not scalable or configurable;

j. prior art cannot provide 100% accurate cyber determinations regarding the identity of any one specific person;

k. prior art cannot be utilized for constantly making accurate cyber determinations regarding the claimed identity of any one specific person;

l. prior art is not configurable for making cyber determinations regarding or utilizing a complete spectrum of analytically rich aspects, characteristics, or features of a complete spectrum of sensor observations or a complete spectrum of sensor observation subjects;

m. prior art does not provide best possible performance for one or more aspects of its operations;

n. prior art is not as operationally concise as it can be in any aspects of its operations;

o. prior art is not as efficient as it can possibly be in any aspects of its operations;

p. prior art is not as simple as it can possibly be in any or all aspects of its operations;

q. prior art lacks the structure that is needed for its operations to be as concise, efficient, and simple as they could possibly be in any or all areas of operations;

r. prior art does not have or use the universal tools, methodologies, or programming that are needed to achieve the highest attainable levels of interoperability in its making of selected cyber determinations regarding or utilizing sensor observations or sensor observation subjects;

s. prior art does not convert sensor observation-derived representations of selected analytically rich aspects, characteristics, or features into standard concise informational representations that can be stored as data or used in prior art's making of selected cyber determinations;

t. prior art does not have or utilize concise datasets to enable the prior art to accurately or reliably make one or more selected cyber determinations without the need for repetitive processing or complex analysis of sensor observations, sensor observation subjects, or sensor observation datasets;

u. prior art is not configurable for making a complete spectrum of selected cyber determinations regarding or utilizing sensor observations or sensor observation subjects;

v. prior art cannot provide the complete spectrum of real-time cyber determinations regarding or utilizing sensor observations or sensor observation subjects that are needed for all the operations of autonomous vehicles or autonomous devices;

w. prior art utilizes machine learning tools, methodologies or programming that are not structured or configured to make selected cyber determinations, and to also provide reports, when needed, regarding why machine learning tools, methodologies, or programming are not performing as intended;

x. prior art cannot typically be configured to use: (i) multiple sensors, (ii) multiple types of sensors, (iii) sensors in multiple environments, or (iv) sensors under multiple operational circumstances;

y. prior art that is utilized in the making of selected cyber determinations regarding or utilizing video-formatted image sensor observations or sensor observation subjects requires the processing of first series observation datasets and second series observation datasets each time a comparison is made of a second series observation or observation subject to a first series observation or observation subject;

z. prior art cannot make a large number of differing real-time cyber determinations regarding or utilizing analytically rich aspects, characteristics, or features of or from sensor observation-derived representations during one cycle of its operations;

aa. prior art is not structured so that the informational representations that are a product of its operations are interoperably usable with other prior art that is utilized for making selected cyber determinations regarding or utilizing sensor observations or sensor observation subjects;

bb. prior art utilizes machine learning tools, methodologies, or programming that are far from being as simple, concise, and efficient as they can possibly be, in part, because prior art fails to recognize, and avoid repeating, any unneeded intermediate cyber determinations that the machine learning tools, methodologies, or programming make during each learning cycle of their operations;

cc. prior art does not separate the operations of processing sensor observations from the operations of making selected final cyber determinations regarding or utilizing sensor observations or sensor observation subjects;

dd. prior art does not create, for further utilization, concise datasets that are the results of its processing of sensor observation datasets;

ee. prior art is not configured to use concise datasets in its making of selected cyber determinations;

ff. prior art is configured to utilize complete original sensor observation datasets for most or all aspects of its making of selected final cyber determinations regarding or utilizing sensor observations or sensor observation subjects; this results in prior art's use of extremely large datasets requiring large amounts of storage, which are difficult, if not impossible to utilize in their entirety in their making of selected cyber determinations. Further, prior art utilizes datasets that are so large that significant processing resources are needed for prior art to constantly provide cyber determinations regarding the identities of specific people (determinations that would be less than 100% accurate);

gg. prior art fails to derive, from its processing of sensor observations, the intermediate cyber determinations that are needed for its making of 100% accurate final cyber determinations regarding the exact identity of any one specific person; and hh. each type of prior art uses its own tools, methodologies, or programming in its making of selected cyber determinations regarding, or utilizing sensor observations, or sensor observation subjects, typically these tools, methodologies, or programming cannot be interoperably used with other prior art in the other prior art's making of selected cyber determinations.

Prior art falls far short of providing the best performing blend of as simple, concise, and efficient as possible. In many ways, prior art provides the worst performing blend of as complex, bloated, and inefficient as it could possibly be in some or all aspects of its operations.

This worst performing blend is due, at least in part, to prior art's failure to employ the structure that is derived from the use of measure points that reliably locate selected analytically rich aspects, characteristics, or features of or from sensor observation-derived representations. Doing so would allow prior art to perform extreme analysis of sensor observation-derived representations at selected points or areas that are reliably located through utilization of measure points.

Prior art methodologies that utilize analysis of entire image-based sensor observations are much more complex and computationally intensive than the utilization of analyzing machine methodologies would be in their making of the same selected cyber determinations.

In light of the foregoing, the disclosed sensor data analyzing machines are configurable for filling the unanswered needs that presently exist with prior art—unanswered needs for selected cyber determinations regarding or utilizing sensor observations or sensor observation subjects that include:

(a) constantly making selected cyber determinations regarding whether or not one specific known person and one specific yet-to-be-identified person are the same person at any selected attainable level of accuracy, including 100% accuracy;

(b) utilizing any necessary number of analytically rich aspects, characteristics, or features of or from one specific known person, or one specific yet-to-be-identified person, in the making of cyber determinations regarding the identity of the one specific yet-to-be-identified person;

(c) utilizing sensor observations of people who are not consciously engaged participants in cyber identity tests;

(d) the making of at least one member selected from the group consisting of: (i) one-time, single event cyber determinations of identity, (ii) intermittently provided cyber determinations of identity, or (iii) constantly provided cyber determinations of identity, regarding people who are subjects of sensor observations;

(e) utilizing sensor observations of a yet-to-be-identified people performing repetitions of selected portions of previously captured sensor observations of known people;

(f) utilizing informational representations regarding sensor observations or sensor observation subjects in the making of selected cyber determinations regarding or utilizing sensor observations or sensor observation subjects;

(g) utilizing analytically rich aspects, characteristics, or features of or from sensor observation-derived representations of a known person or a yet-to-be-identified person in the making of selected cyber determinations regarding the identity of one specific yet-to-be identified person;

(h) utilizing measure points in the locating of selected analytically rich aspects, characteristics, or features o, or from sensor observation-derived representations in the making of selected cyber determinations;

(i) providing, or utilizing standard tools, methodologies, programming, processes, procedures, measurements, designations, informational representations, names, or definitions for accurately or reliably representing any aspects, characteristics, or features of analyzing machines or their operations;

(j) enabling absolute security or privacy for information or resources that are utilized by analyzing machines, or that are utilizing analyzing machines;

(k) utilizing selected criteria for observing, recognizing, locating measure points, assigning appropriate informational representations, storing data, measuring, matching, comparing, determining, reporting, or any other analyzing machine operations;

(l) making selected cyber determinations utilizing observations that were not captured utilizing analyzing machine resources;

(m) utilizing useful information that was derived from sensor observations in the making of selected cyber determinations;

(n) utilizing useful information of any type from any source in the making of selected cyber determinations;

(o) utilizing appropriately assigned standard informational representations regarding, or utilizing measure points or defined points or areas of sensor observation-derived representations that are located through the utilization of measure points; or (p) utilizing appropriately assigned informational representations regarding sensor observations or sensor observation subjects in the making of selected cyber determinations.

The following list includes a portion of the resources, features, or services from a complete spectrum of resources, features, or services that analyzing machines are configurable for providing, including, or utilizing:

(a) cyber determinations regarding or utilizing some or all sensor observation subjects from a complete spectrum of subjects of sensor observations;

(b) cyber determinations regarding or utilizing some or all analytically rich aspects, characteristics, or features of or from sensor observation-derived representations from a complete spectrum of analytically rich aspects, characteristics, or features of or from sensor observation-derived representations;

(c) cyber determinations that fill some or all needs from a complete spectrum of needs for cyber determinations regarding or utilizing sensor observations or sensor observation subjects;

(d) cyber determinations regarding or utilizing sensor observations or sensor observation subjects that are made at one or more selected attainable levels of accuracy, which can include 100% accuracy;

(e) cyber determinations that utilize some or all resources from a complete spectrum of resources that are utilizable in the making of selected cyber determinations;

(f) cyber determinations regarding or utilizing sensor observations or sensor observation subjects that utilize information from a complete spectrum of useful information;

(g) cyber determinations that utilize some or all sensor observations from a complete spectrum of sensor observations;

(h) cyber determinations regarding or utilizing sensor observations or sensor observation subjects that provide for selection of some or all criteria from a complete spectrum useful criteria;

(i) cyber determinations regarding or utilizing sensor observations or sensor observation subjects, wherein analyzing machines utilize: (i) standard processes, (ii) standard procedures, (iii) standard informational representations, or (iv) standard definitions, for accurately or reliably representing any analytically rich aspects, characteristics, or features of or from analyzing machine operations;

(j) cyber determinations regarding or utilizing sensor observations or sensor observation subjects that are made: (i) as one-time events, (ii) intermittently, or (iii) constantly;

(k) testing of identity prior to granting or denying people or cyber devices initial or continued access to: (i) analyzing machines, (ii) cyber resources that are being utilized by analyzing machines, or (iii) cyber resources that are utilizing analyzing machines;

(l) security or privacy, which can include absolute security or privacy for some or all cyber resources or activities that are utilizing, or that are being utilized by analyzing machines;

(m) utilization of sensor observations of any one specific person in the making of selected cyber determinations regarding the identity of the one specific person, wherein the one specific person, who is a subject of sensor observations, is at any point in a range of, from being in the presence of sensors, but not being consciously engaged in determination of identity observations, to being in the observable presence of sensors and being consciously engaged in determination of identity sensor observations;

(n) scalability of included or utilized analyzing machine resources, wherein analyzing machines are configurable for including or utilizing only the analyzing machine resources that are necessary to include or utilize for the making of selected cyber determinations at any point in a range; wherein at the smallest end of the range analyzing machines are configurable for providing for the smallest of all cyber determination needs for included or utilized analyzing machine resources, and at the largest end of the range analyzing machines are configurable for including or utilizing all analyzing machine resources;

(o) ease of use in any or all phases of operations of analyzing machines;

(p) reasonable persistence when attempting to achieve selected goals or any parts thereof;

(q) utilization of observed physical, visual, behavioral, physiological, or biological analytically rich aspects, characteristics, or features of or from sensor observation-derived representations of yet-to-be-identified people or known people when making selected cyber determinations regarding the identities of any specific yet-to-be-identified people;

(r) alteration of the operations of analyzing machines or any resources that are being utilized by analyzing machines, these alterations are made for any useful purpose which includes aiding in achieving possible-to-achieve cyber determination goals;

(s) utilization of useful information that was derived from any source;

(t) appropriately assigning informational representations regarding or utilizing measure points from sensor observation-derived representations;

(u) utilization of unique combinations of analytically rich aspects, characteristics, or features of or from sensor observation-derived representations;

(v) utilization of changes that occur over time to analytically rich aspects, characteristics, or features of or from sensor observation-derived representations;

(w) utilization of combinations of observed analytically rich aspects, characteristics, or features of or from sensor observation-derived representations of sensor observations or sensor observation subjects that were observed over periods of time, or at points in time;

(x) utilization of useful sensor observation data or useful information from any source;

(y) determining or utilizing levels of cyber determination accuracy that have been achieved;

(z) determining or utilizing measures of adequacy of available resources;

(aa) utilizing analyzing machine resources for capturing first series observations or second series observations; or (bb) storing informational representations regarding measure points or analytically rich aspects, characteristics, or features of or from sensor observation-derived representations in concise datasets, wherein the stored data can be utilized in real time or thereafter in the making of selected cyber determinations.

At present we live in a technologically interconnected world where the vast spectrum of available cyber resources is ever-widening. Over time our world appears to be destined to provide every possible cyber resource that humanity could ever want or need. Included in those cyber resources and in accordance with the teachings herein will be scalable, configurable, universal, complete spectrum sensor data analyzing machines that utilize measure points from sensor observation-derived representations or concise datasets in their making of selected cyber determinations regarding or utilizing sensor observations or sensor observation subjects.

Analyzing machines are configurable for utilizing at least one member selected from the group consisting of:

(a) tools, methodologies, or programming for selecting the analytically rich aspects, characteristics, or features of or from sensor observation-derived representations that will be utilized in the making of selected cyber determinations;

(b) tools, methodologies, or programming for identifying the analytically rich aspects, characteristics, or features of or from sensor observation-derived representations that will be located through utilization of measure points;

(c) tools, methodologies, or programming for determining the measure points that will be included as members of standard target sets of measure points, wherein standard target sets of measure points can be configured to be utilized in the making of selected cyber determinations regarding or utilizing selected sensor observations or selected sensor observation subjects under specific sets of, or under varying sets of sensor observation circumstances;

(d) tools, methodologies, or programming for accurately or reliably utilizing measure points in the locating of selected analytically rich aspects, characteristics, or features of or from sensor observation-derived representations;

(e) tools, methodologies, or programming for assigning appropriate informational representations regarding or utilizing at least one member selected from the group consisting of: (i) measure points, (ii) analytically rich aspects, characteristics, or features, (iii) sensor observations, or (iv) sensor observation subjects;

(f) tools, methodologies, or programming for storing informational representations regarding or utilizing at least one member selected from the group consisting of: (i) measure points, (ii) analytically rich aspects, characteristics, or features, (iii) sensor observations, or (iv) sensor observation subjects;

(g) tools, methodologies, or programming for appropriately assigning or utilizing standard informational representations regarding at least one member selected from the group consisting of: (i) measure points, (ii) analytically rich aspects, characteristics, or features, (iii) sensor observations, or (iv) sensor observation subjects, in the making of selected cyber determinations; or (h) any other tools, methodologies, or programming that can be utilized by analyzing machines in their making of selected cyber determinations regarding or utilizing sensor observations or sensor observation subjects.

The disclosed sensor data analyzing machines are configurable for making any cyber determinations regarding or utilizing sensor observations or sensor observation subjects that our world could ever want or need. A further discussion of this universal concept is disclosed in:

(a) co-pending U.S. patent application Ser. No. 16/998,868 (Aronson), filed Aug. 20, 2020, entitled "Universal Operating System", having the same inventor, which is incorporated herein by reference in its entirety; which application is a continuation-in-part application of U.S. patent application Ser. No. 15/483,970 (Aronson), now abandoned, filed Apr. 10, 2017, entitled "Scalable Configurable Universal Operating System", having the same inventor, which is incorporated herein by reference in its entirety; which application is a continuation-in-part application of U.S. patent application Ser. No. 15/236,337 (Aronson), filed Aug. 12, 2016, issued as U.S. Pat. No. 9,660,996 on May 23, 2017, entitled "Point-of-Cyber-Access Cyber System", having the same inventor, which is incorporated herein by reference in its entirety; which application is a continuation-in-part application of U.S. patent application Ser. No. 14/447,283 (Aronson), filed on Jul. 30, 2014, issued as U.S. Pat. No. 9,479,507 on Oct. 25, 2016 (Aronson), entitled "Single-Point-of-Access Cyber System", having the same inventor, which is incorporated herein by reference in its entirety; which application is a continuation application of U.S. patent application Ser. No. 13/702,537 (Aronson), filed on Oct. 19, 2011, issued as U.S. Pat. No. 8,832,794 on Sep. 9, 2014, entitled "Single-Point-of-Access Cyber System", having the same inventor, which is incorporated herein by reference in its entirety; and (b) co-pending U.S. patent application Ser. No. 16/891,088 (Aronson), filed Jun. 3, 2020, entitled "Identity Testing Machine", now pending, having the same inventor, which is incorporated herein by reference in its entirety; which application is a continuation-in-part application of U.S. patent application Ser. No. 16/583,257 (Aronson), filed Sep. 26, 2019, issued as U.S. patent application Ser. No. 10/708,271 on Jul. 7, 2020 entitled "Scalable Configurable Universal Full Spectrum Cyberspace Identity Verification Test", having the same inventor, which is incorporated herein by reference in its entirety; which application is a continuation-in-part application of U.S. patent application Ser. No. 15/456,542, (Aronson) filed Mar. 12, 2017, issued as U.S. Pat. No. 10,462,139 on Oct. 29, 2019, entitled "Scalable Universal Full Spectrum Cyber Determining Process", having the same inventor, which is incorporated herein by reference in its entirety; which application is a continuation-in-part application of U.S. patent application Ser. No. 15/071,075 (Aronson), filed Mar. 15, 2016, issued as U.S. Pat. No. 9,635,025 on Apr. 25, 2017 (Aronson), entitled "Scalable Universal Full Spectrum Cyber Determining Machine", having the same inventor, which is incorporated herein by reference in its entirety; which application is a continuation-in-part application of U.S. patent application Ser. No. 14/857,445 (Aronson), filed Sep. 17, 2015, issued as U.S. Pat. No. 9,319,414 on Apr. 19, 2016, entitled "Scalable Full Spectrum Cyber Determination Process", having the same inventor, which is incorporated herein by reference in its entirety; which application is a continuation-in-part application of U.S. patent application Ser. No. 14/316,196 (Aronson), filed Jun. 26, 2014, issued as U.S. Pat. No. 9,166,981 on Oct. 20, 2015, entitled "Full Spectrum Cyber Identification Determination Process", having the same inventor, which is incorporated herein by reference in its entirety; which application is a continuation of U.S. patent application Ser. No. 13/784,277 (Aronson), filed Mar. 4, 2013, issued as U.S. Pat. No. 8,769,649 on Jul. 1, 2014, entitled "Full Spectrum Cyber Identification Determination Process", having the same inventor, which is incorporated herein by reference in its entirety; which application is a continuation of U.S. patent application Ser. No. 13/688,925 (Aronson), filed Nov. 29, 2012, issued as U.S. Pat. No. 8,434,136 on Apr. 30, 2013, entitled "Full Spectrum Cyber Identification Determination Process", having the same inventor, which is incorporated herein by reference in its entirety.

As the spectrum of available cyber resources grows, so does the need for sensor data analyzing machines that utilize concise, efficient, and accurate real-time tools, methodologies, or programming, and sensor observation data in their accurate or reliable making of selected cyber determinations regarding or utilizing sensor observations or sensor observation subjects.

The more we rely on computing-based resources, the more those resources must be fully automated. In many cases, computing-based resources need to rely on automated real-time cyber determinations regarding occurrences in the physical world to accurately or reliably make the best possible cyber determinations. Analyzing machines are configurable for utilizing best performing blends of: as simple, concise, and efficient operations. Analyzing machines are configurable for doing so, in part, through their utilization of measure points in the locating of selected analytically rich aspects, characteristics, or features of or from sensor-observation-derived representations of sensor observation or sensor observation subjects. Use of measure points or target sets of measure points provides the structure that is needed for analyzing machines to accurately or reliably make selected cyber determinations regarding or utilizing sensor observations or sensor observation subjects.

Analyzing machines are configurable to be at least one member selected from the group consisting of: (a) single, self-contained analyzing machines, (b) analyzing machines that utilize or are utilized by interconnected resources, (c) analyzing machines that are utilized as integral or remote resources of other devices or systems, (d) analyzing machines that are virtual, physical, or combinations thereof, (e) analyzing machines that are stationary, mobile, or combinations thereof, (f) analyzing machines that are utilized by, or utilize devices that are located in one or more locations, or (g) analyzing machines that are utilized by, or utilize interconnected resources.

Best performing is preferably defined as the best possible performance or results that utilization of cyber devices, tools, methodologies, programming, or combinations thereof can achieve. Operations of analyzing machines where best performing can be utilized as a preferred operational goal include: (a) determining which analytically rich aspects, characteristics, or features of or from sensor observation-derived representations will be utilized to simply or efficiently answer selected questions, (b) determining the selections of points or areas of or from analytically rich aspects, characteristics, or features of or from sensor observation-derived representations that will be located through utilization of measure points, (c) capturing first or second series sensor observations, (d) processing sensor observations, (e) locating selected measure points on sensor observation-derived representations, (f) assigning appropriate informational representations regarding or utilizing selected analytically rich aspects, characteristics, or features of or from sensor observation-derived representations, (g) providing structured storage of informational representations regarding or utilizing: (i) sensor observations, (ii) subjects of sensor observations, or (iii) measure points; (h) utilizing measure points that are located on sensor observation-derived representations, (i) assigning or utilizing appropriate informational representations regarding or utilizing sensor observation-derived representations in the making of selected cyber determinations, (j) standardization of at least one member selected from the group consisting of: (i) tools, (ii) methodologies, (iii) programming, (iv) selection of tools, methodologies, or programming to utilize, (v) processing of sensor observations, (vi) storing data, (vii) utilizing data, (viii) selecting of data from sensor observation datasets, (ix) deriving data, (x) assigning or utilizing definitions, (xi) making measurements, (xii) utilization of units of measure, (xiii) making adjustments for differences between first series observations or observation circumstances, and second series observations or observation circumstances, (xix) making selected cyber determinations, (xx) aspects of the operations of analyzing machines from a complete spectrum of other aspects of the operations of analyzing machines, or (xxi) combinations thereof.

Analyzing machines are configurable for the making of selected cyber determinations regarding or utilizing sensor observations or sensor observation subjects by means of matching or comparing informational representations regarding or utilizing yet-to-be-determined analytically rich aspects, characteristics, or features of or from second series observations or second series observation subjects to comparable informational representations regarding or utilizing known analytically rich aspects, characteristics, or features of or from first series observations or first series observation subjects.

Analyzing machines are configurable for having the same outcomes occur every time the same observations are processed as part of first series observation operations, or as part of second series observation operations.

Analyzing machines are configurable for utilizing standard processes or standard procedures to best achieve the goal of same reproducible outcomes from sensor observations of the same subject under differing sensor observation circumstances. As an example, a first series observation is made of a person under a specific set of observation circumstances and standard tools, methodologies, and programming are utilized for assigning appropriate standard informational representations regarding or utilizing sensor observations of the person. When the same person is observed by a different sensor at a different time under a different set of observation circumstances, analyzing machines are configurable for utilizing standard adjusting factors to compensate for the differences in sensor observation circumstances. Analyzing machines use standard adjusting factors to aid in assigning the same standard informational representations to both of the sensor observations of the same person.

Operations of analyzing machines where standard processes, or standard procedures can be utilized in the making of selected cyber determinations include: (a) determining which analytically rich aspects, characteristics, or features of or from sensor observation-derived representations will be located through utilization of measure points, (b) determining which standard target sets of measure points will be utilized for specific observation subjects or observation circumstances, (c) determining which measure points will be included in standard target set of measure points, (d) determining the points on sensor-observation-derived representations where selected measure points will be located, (e) appropriately assigning or utilizing standard informational representations regarding or utilizing analytically rich aspects, characteristics, or features of or from sensor observations or sensor observation subjects, (f) determining the sensors that were utilized in the making of sensor observations, (g) determining matches between informational representations from second series observation concise datasets and comparable informational representations from first series observation concise datasets, (h) deriving informational representations from the processing of first series observation informational representations or second series observation informational representations, (i) utilizing informational representations that were derived from the processing of data from first series observations or second series observations, (j) utilizing standard informational representations or definitions regarding or utilizing a complete spectrum of aspects of the operations of analyzing machines, or (k) utilizing standard units of measure or methods of making measurements in the making of measurements regarding or utilizing sensor observations or sensor observation subjects.

Analyzing machines are configurable for utilizing non-analyzing machine-standard tools, methodologies, or programming. However, informational representations regarding or utilizing sensor observations or sensor observation subjects from non-analyzing machine-standard tools, methodologies, or programming will need to be, either an exact match to, or be translated or adjusted to match the standard informational representations that are assigned or utilized by analyzing machines.

Analyzing machines are configurable for being reasonably persistent in attempting to achieve selected cyber determination goals. As an example, should a selected determination, based upon conclusions from comparing informational representations regarding measure points or analytically rich aspects, characteristics, or features from first series observations of one specific person's face not result in the making of a selected cyber determination of identity, then analyzing machines are configurable for continuing comparing or determining operations until the selected determination has been made or there are no further comparable first series observation concise datasets to compare to available second series observation concise datasets.

The spectrum of sensors or sensor observation data that analyzing machines are configurable for utilizing includes: (a) light sensors that sense any spectra of light, (b) odor sensors, (c) temperature sensors, (d) pressure sensors, (e) energy sensors, (f) image sensors that utilize any spectra of light, (g) odor sensors, (h) chemical sensors, or (i) a complete spectrum of other types of sensor that can be used in the capturing of sensor observations that are utilizable by analyzing machines in their making of selected cyber determinations.

Analyzing machines are configurable for interacting with cyber resources that are being utilized by the analyzing machines. The interacting can be utilized for altering the operations of those cyber resources for any purposes, including to capture any possible sensor observations or providing any useful variations of operations of utilized cyber resources.

Through the incredible speed and power of cyber resources, any large number of criteria can be collectively or selectively utilized for any aspects of the operations of analyzing machines.

All aspects of operations of analyzing machines can be configurable for utilizing selected choices of predetermined criteria. Criteria are selected from a complete spectrum of criteria that can be determined: (a) by people, (b) as an integral part of the operations of cyber resources that are utilizing or being utilized by analyzing machines, (c) as part of the operations of analyzing machines, (d) by utilizing any other means for selecting criteria, or (e) combinations thereof. Selection of any aspect of operations of analyzing machines constitutes selecting criteria.

Criteria are selected choices of who, when, where, what, why, or how as each relates to any aspect of operations of analyzing machines. Providing a choice of any possible criteria and any criteria being possible can well be the most important feature that the entire family of cyber resources has to offer. Analyzing machines are configurable for taking full and best advantage of this particular cyber feature by providing users with choices of selections of available criteria regarding any aspects of utilization of analyzing machines.

Analyzing machines are configurable for utilizing useful information from any source in their making of selected cyber determinations regarding or utilizing sensor observations or sensor observation subjects. Perhaps the most powerful of all useful information that is utilized by analyzing machines when they make selected cyber identity determinations is the information regarding who the one specific yet-to-be-identified person is. If the information that analyzing machines utilize is accurate, then comparison of only one specific person's first series observation concise datasets to the second series observation concise datasets of the one specific yet-to-be-identified person will be all that is needed for accurately or reliably making the selected cyber determination of identity regarding the one specific yet-to-be-identified person.

Analyzing machines are configurable for storing data or datasets utilizing tools, methodologies, or programming from a complete spectrum of tools, methodologies, or programming that are utilized for storing data or datasets.

Analyzing machines are configurable for storing informational representations, as data, utilizing storage media from a complete spectrum of types or variations of utilizable storage media.

Analyzing machines are configurable for storing data or datasets for any duration of time.

Analyzing machines are configurable for standardizing any or all aspects of any or all storage operations or storage resources. Standardization of all aspects of all storage operations or storage resources enables storage operations to be performed at the highest attainable percentages of accuracy, reliability, efficiency, or simplicity.

Analyzing machines are configurable for utilizing data regarding previous same measurements in their making of selected cyber determinations regarding or utilizing changes in same measurements that occur over time. Therein lies one of the more powerful features of the analyzing operations of analyzing machines, selected cyber determinations that are made utilizing changes in measurements or changes in patterns of measurements that occur over time. Measured changes are utilizable by analyzing machines in their making of selected cyber determinations.

Analysis of changes that occur over time is an indispensable part of the accurate or reliable making of a multitude of selected cyber determinations. Many of these cyber determinations cannot be made by prior art because much of prior art is not configured or configurable for making selected cyber determinations that utilize changes to same sensor observations or same sensor observation subjects that occur over time.

Analyzing machines are configurable for performing analysis of sensor observation-derived representations to identify tells that are accurately or reliably utilizable in their making of selected cyber determinations.

Sensor-observable tells that are located through utilization of measure points on sensor observation-derived representations include: (a) distances or changes in distances between measure points, (b) angles or changes in angles where two or more lines between measure points either cross or meet each other, (c) levels or changes in levels of red, green, or blue light at one or more pixels at the locations of, or in areas that are located through utilization of measure points, (d) pressures or changes in pressures at or in the areas of measure points, (e) temperatures or changes in temperatures at or in the areas of measure points, or (f) any other measurable changes to analytically rich aspects, characteristics, or features that are utilizable as tells, wherein the same measurable sensor-observable tells consistently or reliably are present with same or similar specific events, actions, circumstances, or combinations thereof.

Selections of the cyber determinations that are to be made through utilization of sensor observations are made by: (a) tools, (b) methodologies, (c) programming, (d) people, or (e) combinations thereof.

Determinations regarding which analytically rich aspects, characteristics, or features of or from sensor observation-derived representations will be located through utilization of measure points are made by at least one member selected from the group consisting of: (a) tools, (b) methodologies, (c) programming, (d) people, or (e) combinations thereof.

Informational representations regarding or utilizing selected measure points are utilizable by analyzing machines in their making of selected cyber determinations regarding or utilizing at least one member selected from the group consisting of: (a) the locations of selected measure points, (b) a measure point's measured relationship with other measure points, (c) the exact point where a measure point locates analytically rich aspects, characteristics, or features of or from sensor observation-derived representations, (d) areas of analytically rich aspects, characteristics, or features of or from sensor observation-derived representations that are located through utilization of measure points, (e) analytically rich aspects, characteristics, or features of or from sensor observation-derived representations that are separated by lines between two or more measure points, (f) sensor observation-derived representations of odors, (g) sensor observation-derived representations of pressures, (h) sensor observation-derived representations of temperatures, or (i) any other sensor observation-derived representations of analytically rich aspects, characteristics, or features of or from sensor observation-derived representations that are located through utilization of measure points.

Analyzing machines are configurable for utilizing the smallest possible number of informational representations regarding the smallest possible number of selected analytically rich aspects, characteristics, or features of or from the smallest possible number of sensor observation-derived representations as are needed for their making of the smallest possible number of intermediate cyber determinations that are needed for their making of selected final cyber determinations regarding or utilizing sensor observations or sensor observation subjects.

Further, analyzing machines are preferably configured for providing or utilizing concise datasets, wherein the informational representations from concise datasets are as analytically rich as needed for utilization in the making of selected cyber determinations and concise to the point where, if there were any fewer informational representations, it would not be possible to accurately or reliably make selected cyber determinations. Additionally, concise datasets are preferably configurable to include few, if any unnecessary informational representations.

Analyzing machines are configurable for utilizing informational representations from original sensor observation datasets that range from being the least complex, in regard to overall size or complexity, to being extremely complex, in regard to the overall size or complexity. An outdoor light sensor observation is an example of a very small and simple set of informational representations from sensor observations, wherein analyzing machines are configurable for assigning appropriate informational representations regarding the specific times sensor observations indicated a specific threshold high level of light first occurs, and other informational representations are appropriately assigned when a specific threshold low level of light first occurs.

Video-formatted image sensor observations are an example of very large and complex original sensor observation datasets. As an example, a 1080P video-formatted image sensor is configured for providing a stream of thirty sequential two-million pixel images per second. These images have standard information regarding each pixel which includes the pixel's horizontal and vertical line locations, as well as its observed levels of red, green, and blue light.

Analyzing machines are configurable for compressing very large original sensor observation datasets into concise datasets. This practice yields many advantages which include: (a) concise working datasets; as an example, 1080p video sensor observations of a person's face can be compressed down to concise working datasets regarding a standard target set of 17 facial measure points; wherein analyzing machines compress the original sensor observation datasets that are comprised of informational representations regarding more than two-million pixels per image down to concise working datasets that are comprised of sensor data regarding only 17 selected pixels from each image, (b) reduction of the amount of data that is stored or used in the making of selected cyber determinations, (c) reduction in the amount of data that is processed in the making of selected cyber determinations; it is much more efficient to store, process, or use informational representations regarding the 17 pixels at the 17 selected facial measure points than it is to store, process, or use informational representations regarding each of the more than two million pixels that make up the original sensor observation dataset for each video image, (d) many cyber determinations cannot be made by prior art, but they can be made by analyzing machines through their utilization of concise datasets or measure points, or (e) any other advantages that the compressing of very large sensor observation datasets into analytically rich concise datasets enables.

Analyzing machines utilize concise datasets that are comprised of selected sensor data, or derived data.

Selected sensor data are comprised of informational representations that have been selected from original sensor observation datasets by tools, methodologies, programming, or people.

Selected sensor data are preferably configurable for being comprised of the smallest possible amount of data that will be needed for the accurate or reliable answering of selected questions regarding or utilizing sensor observations or sensor observation subjects.

When using selected sensor data regarding only 17 pixels from each sequential video image of a person's face, one might think that this small amount of sensor data would be useless in the making of almost any selected cyber determination. However, with analysis over time, the selected sensor data regarding the 17 pixels is analytically rich, and through utilization of extreme analysis tools, methodologies, or programming, analyzing machines are configurable for deriving a multitude of analytically rich data from the 17 facial pixels, data that are indispensable to analyzing machines in their making of a multitude of selected cyber determinations.

Extreme analysis is the processing of selected sensor data or derived data, wherein the processing results in the creation of derived data that are then included in concise datasets. Further, most, if not all derived data are derived utilizing the extreme analysis tools, methodologies, or programming resources of analyzing machines.

Using one measure point that locates a representation of a pulse point on a sensor observation-derived representation of a person's face as an example, the following determinations can be made: (a) increases in the observed level of red light at the pixel where the pulse point is located can be used for determining every time a pulse occurs, (b) the number of pulses that occur per minute, (c) the average pulse rate for an hour, day, week, during a workout, or when sleeping, (d) using a 23 pixel column or row of pixels that has the measure point at its center, determinations regarding blood pressure can be made, (e) the average blood pressure for an hour, day, week, during a workout, or when sleeping, (f) patterns of changes in pulse rate or blood pressure, (g) changes in patterns of pulse rate or blood pressure over periods of time, including over weeks, months, or years.

These, or other extreme-analysis-derived informational representations can be included as derived data in concise datasets where they can be used by analyzing machines in real time or at times thereafter in the making of selected cyber determinations.

Measure points are usable for purposes from a complete spectrum of purposes for which measure points that are used in the locating of selected analytically rich aspects, characteristics, or features of or from sensor observation-derived representations can be used.

Determinations regarding which measure points or target sets of measure points will be used are made by at least one member selected from the group consisting of: (a) people, (b) tools, (c) methodologies, (d) programming, or (e) combinations thereof.

Measure points provide the structure, continuity, or common elements that are needed to standardize or unify the different operations of analyzing machines when those operations are performed at different times or under the same or different observation circumstances. Through use of the standardization or the structure that is enabled by utilization of measure points, analyzing machines are configurable for utilizing the same standard tools, methodologies, or programming in the making of same or similar selected cyber determinations.

The structure that is provided by utilization of measure points or target sets of measure points enables interoperable use of the disclosed analyzing machine tools, methodologies, or programming across a complete spectrum of analyzing machine systems or environments. Utilization of measure points provides the structure and common elements that are needed to: (a) standardize, (b) unify, or (c) synchronize the operations of the different tools, methodologies, or programming of the disclosed analyzing machines whenever or wherever they are performed.

A spectrum of purposes for which measure points can be used by analyzing machines in their making of selected cyber determinations includes: (a) providing points from which to measure, including measurements of light, temperatures, pressures, colors, odors, chemical signatures, distances, degrees of angles, locations, orientations, times, or any other measurements from a complete spectrum of measurements where measure points can be utilized, (b) locating, on image sensor-derived representations, the corners or boundaries of selected areas of pixels or scalable configurable grids, (c) locating, from image sensor-derived representations, differences or patterns of differences between adjoining pixels that indicate edges or other selected analytically rich aspects, characteristics, or features, (d) being parts of standard target sets of measure points, (e) identifying measure points from standard target sets of measure points whose corresponding analytically rich aspects, characteristics, or features could not be located on sensor observation-derived representations, (f) locating faces on image sensor observation-derived representations, or (g) being used for purposes from a complete spectrum of other purposes for which measure points that are used in the locating of analytically rich aspects, characteristics, or features of or from sensor observation-derived representations can be used.

Measure points can be utilized by analyzing machines in their making of selected measurements, whereby informational representations regarding results of measurements are stored or utilized by analyzing machines in their making of selected cyber determinations. Examples of measurements regarding or utilizing observed analytically rich aspects, characteristics, or features of or from sensor observation-derived representations that are usable by analyzing machines in their making of selected cyber determinations include: (a) measured odors, (b) measured chemical signatures, (c) measured temperatures, (d) measured pressures, (e) measured colors, (f) measured levels of colored light, (g) measured brightness, (h) measured distances between measure points, (i) measured angles where lines between measure points cross or meet, (j) measured speeds, (k) measured time, or (l) any other measurements regarding or utilizing measure points. In addition, analyzing machines are configurable for utilizing changes to selected measurements that occur over time in their making of selected cyber determinations.

Analyzing machine are configurable for determining where to locate measure points on sensor observation-derived representations where they can best be utilized in the locating of sensor-observable changes or tells that reliably occur over any part of a series of sensor observation-derived representations. Analyzing machines are configurable for utilizing selected tells in their making of selected cyber determinations.

Analyzing machines are configurable for utilizing measure points at only the analytically rich aspects, characteristics, or features that are needed for their making of selected cyber determinations.

Determinations regarding which analytically rich aspects, characteristics, or features of or from sensor observation-derived representations will be located through utilization of measure points are made by at least one member selected from the group consisting of: (a) people, (b) tools, (c) methodologies, (d) programming, or (e) combinations thereof.

Guiding factors for determining which analytically rich aspects, characteristics, or features of or from sensor observation-derived representations will be located through utilization of measure points includes: (a) which analytically rich aspects, characteristics, or features of or from sensor observation-derived representations are needed in the making of selected cyber determinations, (b) which sensor-observable changes that occur over time are utilizable in the making of selected cyber determinations, (c) which analytically rich aspects, characteristics, or features that are locatable through utilization of measure points are present or observable in similar sensor observations, or sensor observation subjects, (d) whether all or most similar sensor observations or sensor observation subjects have the same or similar analytically rich aspects, characteristics, or features to locate through utilization of measure points, (e) whether the standard tools, methodologies, or programming of analyzing machines are utilizable for the selecting of the analytically rich aspects, characteristics, or features to utilize, or (f) whether any other factors exist that influence the selection of which analytically rich aspects, characteristics, or features of or from sensor observation-derived representations will be located on sensor observation-derived representations through utilization of measure points.

When utilizing video-formatted image sensor observations of a person's face for making determinations of: "Is the driver of a vehicle falling asleep?", it is only necessary for analyzing machines to utilize two analytically rich features in their making of the selected cyber determinations. The first analytically rich feature is the bottom center of one of the driver's upper eyelids; the second analytically rich feature is the top center of the lower eyelid of the same eye. Analyzing machines utilize measure points in their locating of both of these analytically rich features. The distance between these two measure points is utilized by analyzing machines in their making of selected determinations as to whether or not a vehicle driver's eyelids are closed. Should a driver's eyelids be determined to be closed for a specified duration of time or longer, then analyzing machines are configurable for determining that a vehicle driver is falling asleep, or has fallen asleep. Additionally, should the two measure points drop down together on the pixel grid for a certain distance or more over a certain duration of time, then it is reliably determinable that the person's head has dropped as they nodded off to sleep.

It may be quite easy for a person to determine where measure points should be located on sensor observation-derived representations. As in the previous example, a person's selection of the two specific measure points enabled the analyzing machines to utilize a simple, concise, and efficient combination of sensor-observed behaviors that were compressed into a few standard informational representations that are utilizable, by analyzing machines, in their making of the selected cyber determinations as to whether or not a driver of a vehicle is falling asleep, or has fallen asleep.

Analyzing machines are configurable for selecting and utilizing standard target sets of measure points. Selecting and utilizing standard target sets of measure points is done for the purposes of: (a) including, in standard target sets, only the measure points that might be possible to locate on specific sensor observation-derived representations that are observed under specific observation circumstances; for example, a different standard set of measure points is utilized for a full frontal representation of a person's face than would be utilized for a side view of the same person's face and head, (b) including, in standard target sets, only the measure points that are needed in the making of selected cyber determinations; for example, a standard target set of measure points that are used in the locating of the centers of pupils and the inside or outside corners of eyes is utilizable in the making of selected cyber determinations regarding the direction, in terms of up, down, left, or right, that a person is looking, (c) determining exactly what a person is looking at, (d) locating specific occurrences such as selected increments of time that have elapsed or selected increments of change in temperature that have occurred since the most recent measure point was located on a temperature sensor observation representation, (e) determining which standard target sets of measure points to utilize in the processing of second series observations that will be compared to specific first series observations; wherein in an effort to achieve a highest attainable percentage of cyber determination accuracy, analyzing machines are configurable for utilizing the same standard target set of measure points that were used for first series observations for the analysis of comparable second series observations, or (f) for purposes from a complete spectrum of other purposes for which selecting or utilizing standard target sets of measure points can be used in the operations of analyzing machines.

The points on sensor observation-derived representations upon which selected measure points are located can differ substantially under different observation circumstances. It is therefore necessary for analyzing machines to be configurable for utilizing more than one standard target set of measure points for the same observation, but under differing observation circumstances, with each different standard target set of measure points being configured to enable the accurate or reliable making of selected cyber determinations regarding or utilizing the same or similar sensor observations or sensor observation subjects, but under different observation circumstances.

Determinations regarding which measure points will be included in each standard target set of measure points are made by at least one member selected from the group consisting of: (a) people, (b) tools, (c) methodologies, (d) programming, or (e) combinations thereof.

Analyzing machines are configurable for locating every measure point from a standard target set that can be located. Informational representations regarding measure points from standard target sets that analyzing machines were unable to locate can also be stored or utilized in the making of selected cyber determinations.

Analyzing machines are preferably configurable for utilizing as few target sets of measure points as can possibly be used in their accurate or reliable making of selected cyber determinations; wherein each standard target set of measure points preferably includes as few measure points as could possibly be used by analyzing machines in their accurate or reliable making of selected cyber determinations.

Standard target sets of measure points add the structure that analyzing machines need to process comparable first series sensor observations and second series sensor observations in the same way.

Analyzing machines are configurable for assigning or utilizing standard measurements, standard designations, standard informational representations, or standard definitions to represent observations, subjects of observations, measure points, measurements, or any other analytically rich aspects, characteristics, or features of or from analyzing machines operations.

The appropriate standard informational representations to assign to analytically rich aspects, characteristics, or features are selected by at least one member from the group consisting of: (a) people, (b) tools, (c) methodologies, (d) programming, or (e) combinations thereof.

Standard informational representations that are assigned or utilized include: (a) informational representations identifying the specific sensor observation with which informational representations are associated, (b) informational representations identifying the specific time or times that specific sensor observations, or parts thereof were captured, (c) informational representations regarding the sensors that were utilized in the making of observations, (d) informational representations regarding the circumstances of sensor observations, (e) informational representations regarding which standard target sets of measure points were utilized, (f) informational representations regarding the tools, methodologies, or programming that were utilized, (g) informational representations regarding selected analytically rich aspects, characteristics, or features, (h) informational representations regarding analytically rich aspects, characteristics, or features at the locations of measure points or in areas that are located through utilization of measure points, (i) informational representations regarding measured locations or measured orientations of measure points that are at the exact locations of, or in the areas of selected analytically rich aspects, characteristics, or features of or from sensor observation-derived representations, (j) informational representations regarding measured locations or measured orientations of measure points on sensor observation-derived representation, or in relation to other analytically rich aspects, characteristics, or features that are located by measure points on the same or different sensor observation-derived representation, or (k) informational representations from a complete spectrum of informational representations regarding or utilizing other analytically rich aspects, characteristics, or features of or from measure points, sensor observations, sensor observation subjects, or sensor observation-derived representations.

Utilization of only one standard set of informational representations is an important part of accurately, reliably, and consistently making selected cyber determinations of identity. Analyzing machine identity test are configurable for making, on a worldwide basis, consistent and accurate assignments of standard informational representations to any analytically rich aspect, characteristic, or feature of or from sensor observation-derived representations of people.

Analyzing machines are configurable for utilizing standard adjusting factors to compensate for differences between second series observation circumstances and first series observation circumstances. This includes differences in: (a) lighting, (b) pose, (c) location, (d) movement of sensors, (e) movement of subjects of sensor observations, (f) parts of observation subjects that were observed, (g) wind conditions, (h) sensors that were used for observations, or (i) other differences between second series observations, and first series observations that can be compensated for through utilization of standard adjusting factors.

Typically, analyzing machines break down their processing of sensor observations into three areas of operations: (a) the making of selected initial cyber determinations, (b) the making of selected intermediate cyber determinations, and (c) the making of selected final cyber determinations. In some cases, all or any part of what was determined when making initial cyber determinations will result in the making of at least one selected final determination. Further, the making of any one or more intermediate cyber determinations can also result in the making of one or more selected final cyber determinations. In addition, prior intermediate or final cyber determinations can be utilized in the making of subsequent selected intermediate or final cyber determinations; wherein the previous cyber determinations may have been made, at least in part, to enable the making of one or more subsequent selected cyber determinations.

Analyzing machines are configurable for reporting on or otherwise utilizing results from: initial, intermediate, and final cyber determinations.

Analyzing machines are configurable for providing the highest attainable percentages of simplicity, efficiency, accuracy, or reliability in their making of selected cyber determinations regarding or utilizing sensor observations or sensor observation subjects. They do so, in part, by only performing analysis of the specific sensor observation data that is needed in their making of selected cyber determinations. Therefore, analyzing machines are configurable for not performing analysis of sensor data that is not utilized in their making of selected cyber determinations.

Analyzing machines are configurable for making selected cyber determinations that are not possible to make utilizing measure points from image sensor observation-derived representations. When it is not possible to make selected cyber determinations utilizing measure points, then analyzing machines are configurable for analyzing selected groups of pixels utilizing tools, methodologies, or programming from a complete spectrum of other tools, methodologies, or programming that can be utilized by analyzing machines in their selecting of, locating of, or using of pixels, or groups of pixels.

Analyzing machines are configurable for utilizing three general categories of tools, methodologies, or programming for accurately or reliably locating measure points on sensor observation-derived representations of sensor observation subjects:
  (a) personalized tools, methodologies, or programming that are configurable for accurately or reliably and exclusively locating selected measure points on sensor observation-derived representations of only one specific person or only one other specific observation subject,
  (b) group tools, methodologies, or programming that are configurable for accurately or reliably locating selected measure points on sensor observation-derived representations of any person from specific groups of people or any other observation subject from specific groups of other observation subjects, or
  (c) generalized tools, methodologies, or programming that are configurable for accurately or reliably locating selected measure points on sensor observation-derived representations of any people or any other observation subjects.

Analyzing machines are configurable for achieving highest attainable percentages of accuracy goals when making selected cyber determinations through their use of standard tools, methodologies, or programming that have been trained, taught, or configured for accurately or reliably locating selected measure points on sensor observation-derived representations of only one specific person or only one specific other observation subject. Prior art typically will be trained or taught utilizing a number of different observation subjects that are similar, or that are from a large broad group such as people, or dogs.

Analyzing machines are configurable for providing or utilizing standard tools, methodologies, or programming that are trained, taught, or configured for exclusively locating selected measure points on sensor observation-derived representations of only one specific person or only one specific sensor observation subject. Utilization of personally trained, taught, or configured tools, methodologies, or programming is a necessary part of making selected cyber determinations regarding or utilizing the one specific person or the one specific observation subject at the highest attainable percentages of accuracy or reliability.

Analyzing machines are configurable for locating measure points on sensor observation-derived representations of people, the sensor observation itself, or any other sensor observation subjects, at the highest attainable percentages of accuracy. Analyzing machines locate the measure points through their utilization of tools, methodologies, or programming that are trained, taught, or configured to be utilized for accurately or reliably locating selected measure points on sensor observation-derived representations of one specific person, or one specific observation subject.

The personalized tools, methodologies, or programming of analyzing machines are configurable for brief utilization, wherein the tools, methodologies, or programming learn, or are taught, or configured for the accurate, or reliable locating of selected measure points for a brief period of time, such as, for example, facial identity testing for one-time access to a gym locker.

Two types of basic operations can be used when locating measure points on video-formatted image sensor observations, the first operation utilizes tools, methodologies, or programming for determining the exact initial locations to place selected measure points on one or more sensor observation-derived representations. The second utilizes tracking tools, methodologies, or programming to predict or determining the points where selected measure points are to be located on subsequent sequential sensor observation-derived representations. Should tracking operations be interrupted, then the exact locations of measure points can be determined by performing the processes or procedures that initially determined the locations to place selected measure points.

Analyzing machines are further configurable for constantly or intermittently utilizing initial locating processes or procedures for determining the exact points on each sensor observation-derived representation upon which selected measure points are to be located.

Examples of where analyzing machines may locate measure points on temperature sensor observation-derived representations include: (a) the temperature when a sensor observation begins, (b) the time when a sensor observation begins, (c) any point in time when there is a one degree change from the most recent measure point identified temperature, (d) the temperature when a sensor observation ends, (e) the time when a temperature sensor observation ends, or (f) any other points from temperature sensor observation-derived representations where analyzing machines can utilize measure points in their making of selected cyber determinations.

When analyzing machines are utilized for making selected determinations regarding or utilizing temperature sensor observations, the locating of measure points on sensor observation-derived representation is straightforward; therefore, complex tools, methodologies, or programming are not needed for reliably or consistently locating measure points at 100% accuracy. However, the making of selected cyber determinations that utilize video-formatted image sensor observations of a person's face require utilization of complex combinations of standard tools, methodologies, or programming for accurately or reliably locating or utilizing selected measure points at the highest percentages of accuracy.

Examples of locations where measure points from standard target sets may be located on image-sensor-derived representations of what has been observed by a forward-facing video camera on a vehicle include: (a) perimeters of buildings, (b) perimeters of benches, (c) perimeters of other vehicles, (d) perimeters of people, (e) perimeters of trees, or foliage, (f) edges of sidewalks, (g) edges of curbs, (h) edges of pavement, or (i) other analytically rich aspects, characteristics or features of observation subjects that can be made by a vehicle's video cameras.

Analyzing machine can be configured to utilize windshield-mounted, forward-facing, video-formatted image sensors in their making of selected cyber determinations. Analyzing machines can further be configured to utilize changes that occur in the same informational representations: (a) from sensor observation-derived representation, to sequential sensor observation-derived representation, or (b) over any selected periods of time, in their making of selected cyber determinations regarding or utilizing: (i) the exact location of the vehicle, (ii) the speed that the vehicle is traveling, (iii) the vehicle's location on a roadway in relation to lanes, traffic, other vehicles, pedestrians, curbs or markings, (iv) where to stop, or (v) any other selected cyber determinations that can be made using video-formatted image sensor observations.

Analyzing machines are configurable for utilizing measure points in their locating of selected incremental changes that occur over time to sensor observed analytically rich aspects, characteristics, or features of or from the physical world such as movement, temperatures, pressures, odors, voltage, amperage, sounds, viscosity, speeds, moisture, chemical signatures, or any other sensor-observable analytically rich aspects, characteristics, or features of or from the physical world. Use of concise datasets that only include specific selected incremental changes in sensor observation-derived measurements will typically result in the best performing blend of simple, concise, and efficient as possible means of recording, or utilizing informational representations regarding or utilizing selected analytically rich aspects, characteristics, or features of or from sensor observation-derived representations that occur over time.

Analyzing machines are configurable for utilizing summation table analysis (as later disclosed) in conjunction with scalable configurable grids in their making of selected predictive cyber determinations regarding where to locate selected measure points on subsequent sequential sensor observation-derived representations. Further, analyzing machines are configurable for utilizing smudge analysis (as later disclosed), darkest pixel analysis, lightest pixel analysis, or any methods of analysis, from a complete spectrum of other methods of analysis that can be utilized for predicting or determining where to locate selected measure points on subsequent sequential sensor observation-derived representations.

Utilization of measure points for accurately or reliably locating selected analytically rich aspects, characteristics, or features of or from sensor observation-derived representations is not the only combination of tools, methodologies, or programming that analyzing machines are configurable for utilizing in their making of selected cyber determinations. Analyzing machines are configurable for making selected cyber determinations through utilization of tools, methodologies, or programming from a complete spectrum of tools, methodologies, or programming that can be utilized in their making of selected cyber determinations.

At the heart of most cybersecurity failures is a complete inability of computers or cyber resources to constantly and accurately authenticate the claimed identity of any one specific person prior to allowing that person or the cyber devices of that person to gain initial access and then be allowed to have continued access. Utilizing analyzing machines for accurately and constantly authenticating one specific person's identity as a prerequisite to that person having initial and then continued access to cyber resources is an indispensable step to ending cybersecurity failures.

The key to accurately, or reliably authenticating any one specific person's identity from cyberspace is the utilization of sensor observations of unique physical, visual, behavioral, physiological or biological aspects, characteristics, or features of the person whose identity is being authenticated.

Analyzing machines are configurable for making selected cyber determinations regarding the identity of one specific person (identity tests). These identity tests are utilizable for accurately granting only one specific known person access to their own personal, private, or business cyber resources, thereby preventing all others from gaining similar access.

The key to enabling a high degree of privacy, and security when utilizing cyberspace resources is to require that any one specific person constantly pass their own identity test prior to being granted initial or continued access to their cyberspace resources. Utilizing analyzing machine identity tests, any one specific person can configure all or any part of their own cyber resources to constantly utilize identity testing to always prevent all others from gaining access.

Cybersecurity failures, and the stripping away of each person's personal privacy rights are not the only perils that now plague us from cyberspace. We are also beleaguered by misinformation or disinformation that is delivered throughout cyberspace with malicious intent. Malicious cyber activities include use of ransomware, cyberbullying, and divisive fictitious materials that are posted on social media to name a few. These threats are each enabled by a malicious actor's complete lack of accountability for their activities in cyberspace. Analyzing machines, as configured to provide accurate or reliable constantly performed cyberspace identity testing, are also utilizable for accurately or reliably holding any one specific person accountable for any or all of their own cyberspace activities or resources.

One of the greatest concerns to those who are skilled in the art of providing easy-to-use biologically-based cyberspace identity testing is that the utilized informational representations comprising the cyberspace identity of any one specific person are stolen and then used fraudulently or maliciously. Analyzing machines are configurable for constantly performing cyberspace identity tests for any one specific person, identity tests that no impostor can pass.

Perhaps the most important single task we will soon utilize analyzing machines for will be to constantly provide accurate or reliable cyber determinations regarding any one specific person's identity, both prior to, and during the entire time that the one specific person is using important cyber resources of any type. Analyzing machines, as configured for constantly performing 100% accurate cyberspace identity testing, can be utilized to: (a) end cybersecurity failures, or (b) hold any one specific person accountable for any or all of their cyber resources or their activities in cyberspace.

A technologically interconnected world capable of providing every possible cyber resource humanity could ever want or need can only be built upon the foundation of a secure and safe interconnected cyber environment or cyber ecosystem. Constant utilization of accurate or reliable cyber determinations regarding the identity of any one specific person is an indispensable part of establishing and maintaining a secure and safe cyber environment or cyber ecosystem.

Analyzing machines are a means for providing constant real-time testing of any one specific person's claimed identity for the entire period of time they are using cyberspace resources. One particular standard target set of seventeen facial measure points can be utilized by analyzing machines in their constant testing of any one specific person's identity.

Analyzing machines are configurable for making 100% accurate cyber determinations regarding the identity of any one specific person and they are configurable for doing so utilizing as few or as many unique physical, visual, behavioral, physiological, or biological characteristics of a person as are necessary to achieve attainable cyber identity test goals. When internal and external sensor observations (which can include visual, biological, or physiological sensor observations) of a person are utilized, a very large number of possible unique combinations of analytically rich aspects, characteristics, or features of any one specific person can be utilized by analyzing machine identity tests in their making of cyber determinations of identity. Every unique sensor-observed physical, visual, behavioral, physiological, or biological characteristic of a person is a means for accurately making selected cyber determinations of identity regarding the one specific person.

Using video-formatted image sensor observation of a person's face as an example, analyzing machines accurately or reliably locate a preferred standard target set of seventeen measure points on each sequential sensor observation-derived frontal representation of a person's face from a video stream. One particular selection of locations for 17 facial measure points includes corners of eyes, centers of pupils, bottom centers of upper eyelids, top centers of lower eyelids, tip of nose, centers of left and right jawlines, corners of mouth, top center of upper lip, and bottom center of lower lip.

Utilizing analyzing machine concise datasets regarding the X and the Y line locations of the 17 measure points and the observed levels of red, green, or blue light at each of the 17 pixels where the selected measure points are located enables analyzing machines to constantly make cyber determinations of identity as well as a multitude of other selected cyber determinations regarding or utilizing a person who is the subject of an identity test sensor observation, many of which have not and cannot be made by prior art.

Informational representations regarding any one specific first or second series observation subject can be used as the cyberspace identifiers or the cyberspace identity of the one specific observation subject. These cyberspace identifiers can be used to replace the identifiers that are now used such as social security numbers, birth dates, or driver's license numbers, all of which can be easily stolen or replicated and maliciously used by others.

Analyzing machines are configurable for determining the exact identity of any one specific yet-to-be-identified person, even when there is no knowledge of who the one specific yet-to-be-identified person might be other than the informational representations from second series observation concise datasets of the yet-to-be-identified person. As an example, analyzing machines are configurable for determining the unknown identity of one specific yet-to-be-identified person by utilizing selected criteria that call for utilization of the most unique combination of a person's sensor-observable analytically rich aspects, characteristics, or features for searching available databases of first series observation concise datasets of known people. This search can continue until either one specific known person is found who absolutely is the same person as the one specific yet-to-be-identified person, or no further first series observation concise datasets of comparable known people are available to search or compare.

Should a cyber identity determination, after conclusions from comparing all available informational representations regarding known people, fail to result in the making of a selected determination of identity goal, then analyzing machines are configurable for utilizing additional sensor observations of the one specific yet-to-be-identified person to add to the second series observation datasets of the one specific yet-to-be-identified person for use in further comparisons.

Far more selected cyber determinations can be made about a specific person through utilization of analyzing machine concise datasets regarding the seventeen facial pixels than can be made by prior art through prior art's utilization of the entire two million pixel-per image datasets on which the 17 facial pixels were located.

Analyzing machines are configurable for making selected cyber determinations utilizing available sensor observations. Operations of analyzing machines can begin with selection of which cyber determinations are to be made. Examples of selected cyber determinations that could be made utilizing image sensor observations of a person's face include what is: (a) a person's identity, (b) a person's hair color, (c) a person's eye color, (d) a person looking at on a computer display screen, (e) a person's facial expression, (f) a person's mental or physical state of health, (g) a person's pulse rate, or (h) a person's blood pressure.

Examples of analytically rich aspects, characteristics, or features from sensor observation-derived representations of peoples' faces that can be located through utilization of measure points include: (a) corners of eyes, (b) centers of pupils, (c) tips of noses, (d) corners of mouths, (e) top centers of upper lips, (f) bottom centers of lower lips, (g) tips of chins, (h) edges of jawlines, (i) top centers of eyebrows, (j) outer edges of eyebrows, (k) inner edges of eyebrows, (l) pulse points, (m) scars, (n) marks, or (o) tattoos.

Within a complete spectrum of cyber determinations regarding, or utilizing people as a subjects of sensor observations are a multitude of cyber determinations regarding people including: (a) identity, (b) hair color, (c) moles, (d) wrinkles in skin, (e) freckles, (f) axis points or geometries at joints, (g) scars, (h) height, (i) eye color, (j) pulse rate, (k) blood pressure, (l) blood sugar level, or (m) sensor-observable aspects, characteristics or features of people from a complete spectrum of other sensor-observable aspects, characteristics, or features of people.

Measurements from sensor observation-derived representations can be utilized by analyzing machines in their making of a multitude of selected cyber determinations. One example is the making of selected cyber determinations that utilize facial observations to determine exactly where a person is looking. To do so only requires the use of four measure points that locate four selected analytically rich features from sensor observation-derived representations of a person's face; wherein one measure point is selected to be located at a representation of the center of one pupil and one measure point is selected to be located at a representation of the inner corner of the same eye. These two measure points are utilized by analyzing machines to determine if the person is looking to the left, straight ahead, or to the right, and also to determine if the person is looking up, straight outward, or looking down. The third measure point is selected to be located on a representation of the tip of the person's nose, and the fourth measure point is selected to be located at a representation of the center of their left or right jawline. Distances between the third and fourth measure points are utilized to determine if the person's head is turned to the left, not turned at all, or turned to the right. Further, the difference between the horizontal line location where the measure point at the tip of the nose is located, and the horizontal line location where the measure point at the center of the jawline is located are utilized by analyzing machines for determining if the head is tilted up, not tilted, or is tilted down. Analyzing machines are configurable for utilizing data regarding only the four pixels where the four selected measure points are located for determining precisely where a person is looking.

Rapid eye movement patterns are an example of movements that occur over a short period of time; if certain rapid eye movement patterns are indicators that a person has an intent to do harm, then analyzing machines can utilize observations of a person's eyes that were captured at a rate of 500 frames per second for identifying people who have those rapid eye movement patterns. Analyzing machines can utilize changes that occur over long periods of time, for example, measurements of the range of a person's facial movements over seven years can be used to determine that a person has an early onset of Parkinson's Disease. Analyzing machines can make that determination at the earliest point in time that Parkinson's Disease is sensor detectable. There are a multitude of cyber determinations regarding or utilizing sensor observations or sensor observation subjects that can only be made through utilization of analysis of changes that occur over time, and analyzing machines are configurable for quickly, efficiently, or reliably utilizing measure points or concise datasets in their accurate or reliable making of cyber determinations from a complete spectrum of cyber determinations that can be made regarding or utilizing sensor observations or sensor observation subjects.

Should it be found that specific image sensor-observable rapid eye movement patterns are accurate or reliable indicators that a person has an imminent intent to do harm, then image sensors that capture video-formatted images of a person's eyes at a rate of 500 sequential images each second can be utilized by analyzing machines in their locating of a standard target set of only two measure points. One measure point locates the center of a sensor observation-derived representation of a pupil, and a second measure point locates a sensor observation-derived representation of the inside or outside corner of the same eye. Analyzing machines are configurable for utilizing the horizontal and the vertical line locations, on a pixel grid, of those two measure points in their accurate or reliable making of selected cyber determinations regarding whether or not any one specific person has rapid eye movement patterns that reliably indicate they have an imminent intent to do harm.

Further, the rapid eye movement patterns that might indicate a specific person has an imminent intent to do harm could also be detected using video that is captured at the rate of only 30 or 60 sequential images per second. Analyzing machines are configurable for utilizing smudge analysis in conjunction with scalable configurable grids; wherein one measure point locates a specific point on sensor observation-derived representations where the white of an eye, and the iris meet. Analyzing machines are configurable for performing analysis of patterns of, variations in, or smudges in, observed levels of red, green, or blue light from the area of the sensor observation-derived representations where the measure point is located. As an example, sensor observation data from each pixel within a 15-pixel square that includes the selected measure point at its center could be utilized by analyzing machines in their making of selected real-time cyber determinations as to whether or not any one specific sensor-observed person has an imminent intent to do harm.

Analyzing machines are further configurable for utilizing standard target sets of measure points that comprise only one measure point. This single measure point is utilized for enabling operations of a human fingertip controlled touchless user interface. As an example, a person, using their laptop computer configured analyzing machine, is running their analyzing machine's touchless user interface application. Their laptop-configured analyzing machine's camera captures video at a rate of 30 images per second. The analyzing machine's touchless user interface application is configured for recording, to analyzing machine concise datasets, the horizontal and the vertical pixel grid line locations of the one pixel at the center of the tip of the person's index finger. These operations are performed for each sequential image at a rate of 30 or more images per second. When the person moves their finger, the updated fingertip location is then utilized by their analyzing machine in its real-time updating of the cursor's location on the image display screen.

Concise datasets for touchless user interfaces are derived from each sequential image of a sensor's observations and they may only include data regarding the X and the Y line locations, along with the measured levels of red, green, or blue light at the one pixel.

Analyzing machines are configurable for enabling a person to utilize a video camera to move a cursor or make a selection at the location of the cursor, and they do so without the need for finger-to-touchscreen contact. To make a selection at a current cursor location, all a person needs to do is to move their finger closer to, and then farther away from the camera.

Changes in measured levels of red, green, or blue light at the pixel where the single measure point locates the center of a fingertip are used by analyzing machines for determining that a person wishes to make a selection at the cursor's location.

Examples of prior art human-to-machine interface devices whose full range of functions can be replicated by an analyzing machine's utilization of one, or two fingertips include: (a) mouse interface devices, (b) trackball interface devices, (c) touch screen interface devices, (d) stylus interface devices, (e) keyboard interface devices, or (f) other human-to-machine interface devices whose functions can be replicated through utilization of analyzing machines and a person's intentional movement of their fingertips.

Use of touchless user interface technology is not limited to one fingertip, nor is it limited to fingertips. Touchless user interface applications of analyzing machines can also be configured for utilizing any or all fingertips, the tips of noses, elbows, gaze of eyes, or any other sensor-observable, analytically rich aspects, characteristics, or features of people that can be used to communicate peoples' intentions to interact with analyzing machines, computers, or other cyber devices or resources. Touchless user interfaces can also be configured to offset some or all of disabled peoples' disabilities when interacting with cyber devices or resources.

Working datasets for single-fingertip-controlled touchless user interface applications of analyzing machines are configurable for having the highest amount of compression of data from video images that will ever exist: compression at a ratio of N to one, where N is the total number of pixels that are reported from original video-formatted images, and one is the number of pixels that are reported from the working datasets regarding the one single pixel that a measure point locates at the center of a fingertip; wherein, when using 1080p video, the compression ratio for an analyzing machine's touchless user interface working dataset is over two million-to-one.

Analyzing machines are configurable for being utilized as human-to-machine user interfaces that work in conjunction with cyber devices from a complete spectrum of cyber devices that utilize human-to-machine user interfaces.

The foregoing principles are further appreciated with respect to FIG. 1, which illustrates a first particular, non-limiting embodiment of utilization of one configuration of analyzing machines in accordance with the teachings herein. As seen therein, an analyzing machine 101, is provided which comprises a computing device 103, equipped with an image display 105, and a video-formatted image sensor 107. The computing device 103, has installed, in a tangible, non-transient memory device associated therewith, programming which implements the tools, methodologies, or programming of a human fingertip-to-analyzing machine touchless user interface application. Accordingly, the analyzing machine 101, utilizes the original sensor observation datasets from its image sensor's observations of a person's fingertip in its locating of a measure point, at the one pixel from the image sensor observation-derived representations, that is at the center of each sequential sensor observation-derived representation of the person's fingertip 109. The analyzing machine utilizes the X, and the Y line locations of the pixel as a reference for similarly locating a cursor on the pixel grid of the image display 105. The location of the cursor is updated, from video image, to sequential video image, when there has been a change in the location of the measure point on the sensor observation-derived representation's pixel grid. The person makes a selection at the location of the cursor by quickly moving their fingertip closer to, and then farther away from the image sensor. Changes in measurements of observed levels of red, green, or blue light at the pixel where the measure point is located enable the analyzing machine to determine that the person wishes to make a selection where the cursor is located on the image display screen. In this particular depiction the user's finger is utilized as an alternative to a mouse or stylus for drawing purposes, although it will be appreciated that the same or similar techniques can be utilized for a wide variety of other purposes.

The concise, efficient, and simple tools and methodologies of touchless user interfaces are also utilizable for accurately authenticating the identity of any one specific person. One example of how analyzing machines perform identity authentications requires a person to sign their name in the air for observation by a video camera. Many factors are utilized for comparing a specific yet-to-be-identified person's signature to the signature of any one specific known person that the yet-to-be-identified person claims to be. Analytically rich aspects, characteristics, or features that are utilized by analyzing machines in their making of the selected cyber identity authentication determinations include: (a) the line pattern of the signature, (b) behavioral characteristics of movement, including movement toward and away from the camera, (c) cadence, (d) speed, or (e) timing. Utilizing comparison of second series observation signatures to first series observation signatures enables the making of selected cyber identity determinations at the highest attainable percentages of accuracy or reliability. Utilization of the movement of only one fingertip-located measure point is one method that analyzing machines can be configured for providing 100% accurate identity authentication. This simple methodology can be used to eliminate payment fraud, and analyzing machines perform the identity authentications utilizing methodologies that are as simple, concise, and efficient as possible.

Analyzing machines are configurable for making selected cyber determinations that have not been made or cannot be made by prior art. Further, analyzing machines are configurable for performing processes or procedures that are as simple, concise, efficient, and accurate as possible.

The tools, methodologies, and programming that are utilized by analyzing machines operate differently than the tools, methodologies, and programming of prior art, yet analyzing machines are utilizable for making the same selected cyber determinations as can be made by prior art. Analyzing machines do so, in part, by using tools, methodologies, and programming that utilize measure points in the locating of selected analytically rich aspects, characteristics, or features of or from sensor observation-derived representations. Analyzing machines also utilize concise datasets that are configured or structured for consistently being utilizable in the making of accurate or reliable cyber determinations under same, similar, or differing sensor observation circumstances. Additionally, analyzing machine tools, methodologies, or programming are configurable for being easily diagnosed, repaired, or operationally altered if needed.

Analyzing machines are configurable for utilizing their tools, methodologies, or programming in the making of selected cyber determinations; wherein measure points that are used in the locating of selected analytically rich aspects, characteristics, or features are also utilized by analyzing machines for establishing or maintaining the structure that is needed for consistently locating, through utilization of measure points, selected analytically rich aspects, characteristics, or features of or from sensor observation-derived representations. Analyzing machine tools, methodologies, or programming are configurable for being utilized for operational purposes including: (a) grouping measure points into standard target sets of measure points, (b) determining which analytically rich aspects, characteristics, or features of or from sensor observation-derived representations are to be located through utilization of measure points, (c) locating selected measure points on sensor observation-derived representations, (d) assigning appropriate informational representations to selected analytically rich aspects, characteristics, or features of or from sensor observation-derived representations, (e) storing selected informational representations in the structured environments of analyzing machine concise datasets, (f) utilizing informational representations from analyzing machine concise datasets in the making of cyber determinations, or (g) for purposes from a complete spectrum of other operational purposes for which analyzing machines can be utilized.

Analyzing machines are configurable for achieving the highest attainable percentages of simplicity, efficiency, accuracy, or reliability through their utilization of selected measure points, standard target sets of measure points, concise datasets, standard tools, methodologies, or programming in their providing of selected cyber determinations regarding or utilizing sensor observations or sensor observation subjects.

In some instances, informational representations regarding selected analytically rich aspects, characteristics, or features of or from sensor observation-derived representations need to be intermittently or constantly updated with the most recent informational representations regarding: (a) measure points, or (b) analytically rich aspects, characteristics, or features of or from sensor observation-derived representations. As an example, a person, who has very light-colored eyebrows, uses an eyebrow pencil several times a day to give their eyebrows a more distinct visual presence. There are slight changes to the locations of the eyebrows each time the eyebrow pencil is applied. Analyzing machines are configurable for making appropriate changes to selected informational representations regarding the measure points that are utilized in the locating of a person's eyebrows every time the person applies eyebrow pencil.

Analyzing machines are further configurable for utilizing measure points in their making of selected cyber determinations regarding or utilizing the measured locations or the measured orientations of selected analytically rich aspects, characteristics, or features of or from sensor observation-derived representations of sensor observations or sensor observation subjects.

Examples of cyber determinations regarding the measured locations or the measured orientations of selected analytically rich aspects, characteristics, or features of or from sensor observation-derived representations include: (a) measured locations or measured orientations of sensor observation-derived representation of scars on sensor observation-derived representations of people, (b) measured locations or measured orientations of sensor observation-derived representations of marks on sensor observation-derived representation of people, (c) measured locations or measured orientations of sensor observation-derived representations of tattoos on sensor observation-derived representations of people, (d) measured locations or measured orientations of sensor observation-derived representations of fingerprint features on sensor observation-derived representations of peoples' fingers or fingerprints, or (e) measured locations or measured orientations of analytically rich aspects, characteristics, or features of or from sensor observation-derived representations, from a complete spectrum of analytically rich aspects, characteristics, or features of or from sensor observation-derived representations of sensor observations or sensor observation subjects.

Analyzing machines are configurable for providing or utilizing scalable configurable grids in their making of initial cyber determinations, intermediate cyber determinations, or final cyber determinations.

Using a video camera observations of a person's face as an example, analyzing machines are configurable for comparing patterns of observed levels of red, green, or blue light at each of the pixels from within scalable configurable grids. In this example, scalable configurable grids are used to define areas of pixel-based sensor observation-derived representation where it is anticipated that the measure point that locates the tip of a person's nose will accurately or reliably be located. Patterns of observed levels of red, green, or blue light are analyzed utilizing tools, methodologies, or programming from a complete spectrum of tools, methodologies, or programming that are utilizable by analyzing machines in their determining of where selected measure points will be located on the pixel grids of sensor observation-derived representations.

Scalable configurable grids can be square, rectangular, round, oval, or irregularly-shaped.

Analyzing machines are configurable for performing analysis of all or parts of the pixels from within scalable configurable grids.

Two or more pixels are present within each scalable configurable grid.

Scalable configurable grids utilize, scale to, or conform with the pixel grids of sensor observation-derived representations.

Measure points can be regularly located, for example, at 10, 50, or 100-pixel distances apart on both the X and the Y axes of pixel grids to form a plurality of groups of pixels from within a plurality of scalable configurable grids Groups of pixels can be a selected subject of analysis; wherein results from analysis are usable in whole or in part by analyzing machines in their making of selected cyber determinations. Adjoining or overlapping scalable configurable grid-defined groups of pixels are combinable; wherein the combined groups can be utilized by analyzing machines in their making of selected cyber determinations.

Scalable configurable grids are configurable for providing the structure that is needed for performing repeated analysis of the same specific selected areas of pixels from each comparable image sensor observation-derived representation that is used by analyzing machines in their making of selected cyber determinations.

Additionally, analysis of what was observed from within scalable configurable grids can be performed at increasing or decreasing levels of detail as needed. Similarities or differences between informational representations from differently scaled scalable configurable grids can be utilized by analyzing machines in their making of initial cyber determinations, intermediate cyber determinations, or final cyber determinations.

Analyzing machines are configurable for utilizing tools, methodologies, or programming from a complete spectrum of tools, methodologies, or programming that can be utilized in their making of selected cyber determinations regarding or utilizing groups of pixels. Analyzing machines are also configurable for using tools, methodologies, or programming from a complete spectrum of tools, methodologies, or programming that can be utilized by analyzing machines in their making of selected cyber determinations regarding, or utilizing groups of pixels that are located through utilization of one, or more measure points.

Analyzing machine summation table tools, methodologies, or programming are utilizable in combination with scalable configurable grids in the making of selected cyber predictions, or determinations regarding where measure points will be located on current or on upcoming sequential sensor observation-derived representations. Summation tables are configurable for utilizing scalable configurable grids as the structures that aid in their accurate or reliable locating of the same aspects, characteristics, or features from every comparable image sensor observation-derived representation.

Summation table analysis is configurable for utilizing the sums from all or parts of columns or rows of measurements of observed levels of red, green, or blue light from within scalable configurable grids; wherein analyzing machines use sums from summation analysis in their making of selected cyber determinations.

The sums of measured levels of red green, or blue, light that were observed from all or parts of columns or rows from pixel grids can be determined and utilized by analyzing machines in their making of selected cyber determinations. Additionally, any combinations of sums from all or parts of columns or rows from within scalable configurable grids are utilizable for purposes from a complete spectrum of purposes for which sums of measurements of observed levels of red, green, or blue light from columns or rows from within scalable configurable grids can be utilized. One such utilization is the efficient locating of one specific person's face from video-formatted image sensor observation-derived representations.

Analyzing machines are configurable for utilizing summation table analysis for determining how many pixels that selected aspects, characteristics, or features have moved from their relative locations in previous sequential sensor observation-derived representations.

Prior art facial recognition processes or procedures dedicate the largest percentage of their processing to finding faces. Analyzing machines are configurable for comparing second series observation summation table analysis of a person's face to first series observation summation table analysis of a person's face; wherein analyzing machines utilize informational representations from first series observation summation table analysis of a person's face in their efficient locating of the same person's face from second series observations.

Utilizing informational representations from summation table analysis of any one specific known person in the finding of that specific person's face from video-formatted image sensor observation-derived representations will result in profound increases in operational efficiencies over prior art. Further, the same summation table-derived informational representations are usable as an initial cyber test of any one specific person's identity. Should it not be possible to use first series summation table informational representations to find the face of a specific first series observation subject from second series observation-derived representations, then the second series observation subject is unlikely to be the person from the first series observations that they claim to be.

Analyzing machines are configurable for accurately or reliably determining that the center of a measure point will be located one-half of a pixel up and one-third of a pixel to the right on the pixel grid of the next sequential sensor observation-derived representation. This is determined through their utilization of the tools, methodologies, or programming that perform smudge analysis. Analyzing machines are configurable for performing analysis of patterns of smudges from image sensor observation-derived representations in which analysis of measured levels of red, green, or blue light, or any other colors of light from a complete spectra of colors of light that can be utilized for accurately or reliably: (a) indicating the presence of remnants of light that were fully present prior to the exact point in time that an image was captured, or (b) utilizing light from adjoining areas that has reflected or refracted upon specific pixels or specific areas of pixels. Analyzing machines are configurable for utilizing analysis of observed presences of remnants of light, reflected light, or refracted light in their making of cyber determinations from a complete spectrum of cyber determinations regarding or utilizing sensor observations or sensor observation subjects where remnants of light, reflected light, or refracted light are observed.

When viewing a piece of black electric tape that is affixed to a piece of white paper, one might assume that the color of the pixels at the precise edge where the black tape and the white paper adjoin would be black on the tape side and white on the paper side. However, sensors that are used to capture images of the tape and paper do not capture images with those results. Light from the black, and light from the white impose on each other where black and white adjoin. The imposing of colored light from one pixel to another is due, at least in part, to the reflective or refractive properties of light. The highest level of the imposition occurs at the edge where the black and the white meet as evidenced by the color values for the black, which are lightest at the point where the two colors meet, and the color values for the white, which are darkest at the point where the two colors meet. If an image sensor and the paper and tape are stationary while the image is being captured, then there will usually be a clean graduation of, or mixing of color where black meets white. Should there be no movement of the sensor or the tape and paper, then analysis of the point where tape and paper adjoin will result in the same graduated change of color from each sequential image. Should there be movement of the image sensor or the tape and paper when the sensor observation is captured, then a smudge or smudges in the graduated colors, or an elongation of the graduated colors are reliably observed. The smudge or smudges can be used by analyzing machines for purposes from a complete spectrum of purposes for which smudges from sensor observation-derived representations can be utilized. One such utilization would be to predict directions and distances of movement, from a current image's pixel grid to the next sequential image's pixel grid.

Another utilization of smudge analysis is for determining the distance and the direction of movement that occurs from one sensor observation-derived representation to the next sequential representation when observed movement between images is less than one pixel in distance. Through utilization of smudge analysis, the amount that any of the colors of observed light from one pixel infringe or impose on differently colored light from adjoining pixels is usable by analyzing machines in their making of selected cyber determinations regarding the distance or direction of movement, in fractions of a pixel, that selected analytically rich aspects, characteristics, or features have moved on a pixel grid since the previous sensor observation-derived representation.

In one scenario, a "known person" has a laptop-configured analyzing machine. An analyzing machine identity test application is an integral resource of the known person's analyzing machine. The analyzing machine identity test is utilized, in part, for making determinations of identity that are utilized for exclusively granting only the known person access to further use of their analyzing machine, and its resources. The laptop-configured analyzing machine includes a video camera that has adjustable pan, tilt and zoom functions that can be operated by the analyzing machine's identity test.

The analyzing machine identity test captures and processes sensor observations of the known person, the results of which are stored as the known person's first series observation concise datasets. The first series observation concise datasets of the known person are exclusively made of informational representations regarding the known person. Informational representations that makes up the known person's first series observation concise datasets are utilizable as the known person's cyberspace identity, or identifiers.

A cycle of utilization of the analyzing machine identity test is initiated by a yet-to-be-identified person requesting use of the known person's analyzing machine.

In the instance of this cycle of utilization, the analyzing machine identity test utilizes the camera to capture video-formatted images of the yet-to-be-identified person. To provide observations that would be the most likely to aid in the making of selected cyber determinations of identity, the analyzing machine identity test operates the zoom function of the camera to closely frame images of only the face of the yet-to-be-identified person.

As a part of either series of observations, analyzing machine identity tests are configurable for locating a standard target set of measure points at specific selected points on image sensor-observation-derived representations of peoples' face. The analyzing machine identity tests are configurable for utilizing the X and the Y line locations on pixel grids, or the observed levels of red, green or blue light from each pixel where selected measure points are located in their making of selected cyber determinations.

Analyzing machine identity tests are further configurable for assigning appropriate informational representations, from a standard set of informational representations, to selected analytically rich aspects, characteristics, or features of or from sensor observation-derived representations of yet-to-be-identified people.

Appropriate informational representations that accurately or reliably represent the selected analytically rich aspects, characteristics, or features of or from representations of yet-to-be-identified peoples' face are assigned, and then included in the yet-to-be-identified peoples' second series observation concise datasets.

In the instance of this cycle of the utilization of the analyzing machine identity test, predetermined criteria call for selecting comparable datasets from first series observation concise datasets of the known person. Further, first series observation concise datasets are selected because they are the most likely of all available first series observation concise datasets to aid in the accurate or reliable making of selected cyber determinations as to whether or not a yet-to-be-identified person and the known person are the same person.

The analyzing machine identity test utilizes criteria that includes time, date, temperature, light sources, light levels, and the observed portion of the yet-to-be-identified person in its matching of second series observation concise datasets with comparable first series observation concise dataset of the known person.

Analyzing machines are configurable for making final determinations regarding many analytically rich aspects, characteristics, or features of or from sensor observations or sensor observation subjects during their assigning of appropriate informational representations. For example, when informational representations were assigned, final determinations were also made that the person who was the subject of the sensor observation had red hair, hazel eyes, a particular geometry and ratio of movement between joints while opening or closing fingers, as well as many other physical, visual, behavioral, physiological, or biological characteristics.

Further, when utilizing observations with more than one person as a subject, analyzing machines are configurable for excluding, from further determinations, any person who is a subject of the observation who has been determined to not fit certain parameters. For instance, in keeping with the previous example, analyzing machines are configurable for excluding from further processing, any person who has been determined to have hair that is not red or eyes that are not hazel. Also, based upon predetermined criteria, one specific yet-to-be-identified person is determined to absolutely not be the same person as the one specific known person if it is determined that the yet-to-be-identified person did not have red hair or hazel eyes.

Matched observation datasets of the yet-to-be-identified person and the known person are compared by the analyzing machine identity test.

Conclusions from comparing informational representations from first and second series observations, along with useful information, are utilized by the analyzing machine identity test in its making of selected cyber determinations.

In this instance, the analyzing machine identity test compares informational representations from second series observation concise datasets to informational representations from first series observation concise datasets wherein both first series and second series observation concise datasets are comprised of informational representations regarding or utilizing only the pixels where selected measure points are located, or selected pixels that are in areas that are located through utilization of measure points. Analyzing machine identity tests are configurable for making adjustments, as a part of their comparing operations, for differences in observation circumstances or other differences between first series observations and second series observations.

Comparison of second series observation concise datasets to first series observation concise datasets provides an overabundance of physical, visual, behavioral, physiological, or biological characteristics that are utilizable in the accurate or reliable making of selected cyber determinations of identity. Far more comparable analytically rich aspects, characteristics, or features exist than are needed for making the selected cyber determinations, with 100% accuracy, that a yet-to-be-identified person and a known person absolutely are the same person.

Once the selected cyber determinations have been made, the analyzing machine identity test is configurable for reporting on the determinations.

The determination that the yet-to-be-identified person and the known person absolutely are the same person is reported to analyzing machine history and also to programming running on the laptop computer-configured analyzing machine. Having received the real-time report from the operations of the analyzing machine identity test that the yet-to-be-identified person absolutely is the same person as the known person, the analyzing machine then grants the known person exclusive access to use of its resources. History or any other aspects of the operations of analyzing machines disclosed herein are stored in volatile or non-volatile memory, e.g., in storage modules that are utilized by computers.

To best demonstrate selected further utilizations of the analyzing machines disclosed herein, it is helpful to consider future technologies such as Single-Point-of-Access Cyber Systems or Point-of-Cyber-Access Cyber Systems. Single-Point-of-Access Cyber Systems, and Point-of-Cyber-Access Cyber Systems enable technologically interconnected cyber environments or cyber ecosystems that are configurable for enabling the full and the best utilization of the disclosed analyzing machines.

To begin, Single-Point-of-Access Cyber System architecture and Point-of-Cyber-Access Cyber System architecture both provide people with remotely located point of cyber access computer-analyzing machines. People can utilize any mobile or stationary terminal-type of device that is called a cyber portal to gain secure and private access to their own point of cyber access computer-analyzing machine.

Each person's own remotely located point of cyber access computer-analyzing machine is utilizable in the making of selected cyber identity determinations regarding people at levels of accuracy that include 100% accuracy.

In this example, a cycle of utilization of an analyzing machine identity test is initiated when a yet-to-be-identified person utilizes a cyber portal to contact, and request access to the personal or private resources of a known person's remotely located point of cyber access computer-analyzing machine.

Each person's point of cyber access computer-analyzing machine is configurable for only allowing access to its proprietary user, the one specific known person, and only after a yet-to-be-identified person has, with 100% accuracy, been determined to be the proprietary user of that specific point of cyber access computer-analyzing machine. In this instance, the known person's point of cyber access computer-analyzing machine is further configured to require constant authentication of the known person's identity during the entire time that the known person is utilizing its resources.

In this example 100% accuracy is achieved and the yet-to-be-identified person has been determined to absolutely be the same person as the proprietary user of the point of cyber access computer-analyzing machine. This identity determination must be made before the previously yet-to-be-identified person is granted initial and continued access to the personal and private resources of their own remotely located point of cyber access computer-analyzing machine.

In one non-limiting embodiment, a cyber portal, utilizing its integral camera, captures observations of a yet-to-be-identified person. The sensor observation dataset from the yet-to-be-identified person is communicated to a remotely located point of cyber access computer-analyzing machine. The point of cyber access computer-analyzing machine, utilizing tools, methodologies, or programming that are trained, taught, or configured to be used for or by only one specific person, utilizes informational representations from video datasets in its making of selected cyber determinations regarding the identity of the person who is using the remotely located cyber portal.

Analyzing machine identity tests are configurable for controlling operations of pan, tilt, zoom, or focus functions of video cameras. This capability is used for capturing optimum second series observations of yet-to-be-identified people.

Analyzing machine identity tests are configurable for utilizing measure points in their accurate or reliable locating of selected analytically rich aspects, characteristics, or features of or from image sensor-observation-derived representations of a yet-to-be-identified person's face. Informational representations regarding the X and the Y line locations on a sensor observation-derived representation's pixel grid, along with measurements of observed levels of red, green, or blue light at or in the areas of pixels where selected measure points are located, are matched or compared to informational representations from first series observation concise datasets of the known person who is the proprietary user of the point of cyber access computer-analyzing machine.

Analyzing machine identity tests are configurable for utilizing standard adjusting factors for accurately, or reliably making selected cyber determinations when there are differences in observation circumstances, or differences in other circumstances between first series observations, and the second series observations to which they are being compared.

Single-Point-of-Access Cyber Systems or Point-of-Cyber-Access Cyber Systems require a person be accurately determined to be the proprietary user of their point of cyber access computer-analyzing machine before they can gain initial access to its personal or private resources. Single-Point-of-Access Cyber Systems or Point-of-Cyber-Access Cyber Systems preferably require a known person be constantly determined to be its proprietary user when they are using their own point of cyber access computer-analyzing machine.

The analyzing machine identity test enabled, secure, safe, and private technologically interconnected cyber environment or cyber ecosystem of Single-Point-of-Access Cyber Systems or Point-of-Cyber-Access Cyber Systems are utilizable for providing the planet with vast new cyber resources. Among those resources will be devices that utilize sensors for regularly or constantly monitoring selected aspects of a person's health.

Point of cyber access computer-analyzing machines are fully utilizable through use of cyber portals that are similar in size and are worn similarly to a wristwatch. Although cyber portals with image display screens of such a small size can require intermittent use of a larger image display screen, wristwatch-configured cyber portals can nonetheless provide the greatest all-around utility of cyber portal configurations, in part because wristwatch-configured cyber portals that include health metrics sensors can be utilized for securely and privately monitoring and reporting, to one's point of cyber access computer, any possible sensor-derived health observations (both internal and external).

A person's own point of cyber access computer-analyzing machine can then utilize those health observations for providing the person (perhaps through use of their wristwatch-configured cyber portal), reports of any health information that the person may want or need to utilize or be made aware.

Through utilization of the security, safety, and privacy that is enabled by the cyber determinations of identity that are made by analyzing machine identity tests and the resources of Single-Point-of-Access Cyber Systems or Point-of-Cyber-Access Cyber Systems, it will be possible to securely and privately provide all or part of a person's own personal and private health information to health care practitioners of choice. Doing so should enable the practitioners to provide the person with the best possible health care treatments or outcomes.

It will also be possible for a person to anonymously provide all or part of their health records to selected others for use in health-related research.

Utilizing a wristwatch-configured cyber portal/health metrics monitor, each person can enjoy the benefits of secure and private uninterrupted observations of any number of measures of their health.

When the previous continuation-in-part disclosure was written, the World was experiencing the initial ravages of the COVID-19 pandemic. Beyond loss of life and ill health, the pandemic initially resulted in lost jobs, lost revenues, failed businesses, and financially devastated lives. Perhaps widespread use of analyzing machines that were configured to be used, in whole or part, as COVID-19 monitors or as sensor observation-derived COVID-19 tests, could have enabled far better control of the virus's initial spread and lessened unwanted consequences.

Analyzing machines are configurable for being utilized as universal health metrics monitors that can constantly monitor a person's stream of health sensor data for known health metrics or health metrics patterns that are reliable indicators of: (a) an onset of an adverse health occurrence, (b) adverse health occurrences that are occurring, (c) adverse health occurrences that have occurred, (d) intermediate stages a person's cycles of adverse health occurrences, (e) when a person is no longer contagious, or (f) the end of a person's adverse health occurrence.

Universal health metrics monitors disclosed herein are configurable for being utilized as continuous, real-time, 24/7 monitors that reliably detect that a person is infected with COVID-19, preferably before the infected person is contagious. Instantaneous real-time alerts, from universal health metrics monitors, would enable infected people to contact health care providers and self-quarantine right away, thereby significantly limiting or stopping spread of the virus.

Universal health metrics monitors can be further configured to monitor a person's health through the entire cycle of their infection. Universal health metrics monitors can also be configured to make reports that infected people are no longer contagious. Early knowledge that people are infected, along with knowledge of exactly where people are in their cycle of infection, would be valuable tools in providing the best possible health-related treatments and outcomes.

Knowing a person is no longer contagious would allow that person to end quarantine and safely go back to their usual life. In addition, all those who were not found to be infected with the virus could safely go about their lives with the security of knowing they will be instantly alerted should their universal health metrics monitors detect they are infected with COVID-19. Allowing those who are not infected or those who were infected, but were no longer contagious to safely go about their regular lives would be far better than the methodologies that have been used.

Universal health metrics monitors are configurable for monitoring intermittent or continuous streams of sensor data for changes in health metrics data that only occur with people who are known to be infected with COVID-19. Once these are discovered, the changes (tells) from the streams of health metrics data can then be utilized to determine the need to alert the person that they have a COVID-19 infection. In addition, this same simple methodology can be utilized to provide infected people with interactive alerts at various stages in the cycle of their COVID-19 infections.

Examples of sensor-observable occurrences that could be reliable indicators that a person is infected with COVID-19 include: (a) patterns of movement from coughing or shivering, (b) changes in body temperature, (c) patterns of changes in body temperature, (d) changes in average blood oxygen levels, (e) changes in patterns of blood oxygen levels, (f) changes in patterns of respiration, (g) changes in patterns of blood oxygenation levels during respiration, (h) changes in average blood oxygenation levels, (i) changes in patterns of blood oxygenation levels, (j) the presence of odors or chemical signatures that only occur during COVID-19 infections, (k) facial affect, (l) the sounds of respiratory abnormalities, or (m) combinations thereof.

The same processes or procedures that were used for discovering the sensor-observable tells of a COVID-19 infection can also be used by the universal health metrics monitors for discovering sensor-observable tells for any adverse health issue from a complete spectrum of sensor-observable adverse health issues.

As one non-limiting example of use, data streams from odor or chemical sensors are utilized by universal health metrics monitors for identifying and then reporting on an observed presence of specific odors or chemical signatures that reliably indicate a person has an abnormal cancer cell count. Use of intermittent, or constant monitoring for the earliest sensor-detectable specific odors or chemical signatures that reliably indicate an abnormal cancer cell count has occurred may be the key to ending cancer-related illness.

Prior art in the field of healthcare typically utilizes one-time analysis or testing of a person for making health-related determinations or diagnoses. Universal health metrics monitors introduce and enable the use of intermittent or continuous 24/7 monitoring or recording of a person's health metrics. If knowledge is power, then the knowledge that will be gained by the continuous monitoring or recording of peoples' health metrics may well be the catalyst for the most profound healthcare advancement we will see. One of the advancements will be the discovery of tells that reliably indicate adverse health issues have occurred or will soon occur. The tells will be found by determining what all people who have had the adverse health occurrence have in common in concerning changes, or changes in patterns of their health metrics data that only occur with a common adverse health occurrence. As an example, should everyone who has a heart attack or stroke experience the same changes or patterns of changes in their health metrics three days or three hours prior to their adverse health occurrence, then universal health metrics monitors can be configured to monitor a person's stream of health metrics data for the specific changes or patterns of changes that reliably indicate a person will have a heart attack or stroke, and alert the person when the reliable indicators are observed.

Using a previous example, sensor-detectable odors or chemical signatures may soon be used to reliably indicate a person has an abnormal cancer cell count. Some portion of the people who have the onset of this sensor-observed adverse health occurrence will find that it does not persist and quickly goes away. Possibly commonalities exist between the members of this group, such as they all drank glasses of fresh orange juice. This discovery could lead to a treatment of drinking a glass of fresh orange juice when they are notified by their health metrics monitor that an abnormal cancer cell count has been observed. This concept for discovering cures is universally usable for any adverse health occurrences that have been detected by universal health metrics monitors and then disappears without prescribed intervention.

Another example of the power that knowledge from use of universal health metrics monitors will enable is in the area of maintaining optimal health metrics. At present little is known about optimal health metrics or how to maintain optimal health metrics throughout a person's lifetime. Additionally, very little is known about the effects that having less than optimal health metrics plays in our mental or physical health or well-being. Universal health metrics monitors are configurable for helping a person achieve and maintain optimal health metrics for the remainder of their life. Optimal health metrics will be unique to each person and the health metrics monitors disclosed herein are configurable for being utilized as personalized tools that will enable people to achieve any attainable level of optimal health metrics through activity or management of their intake of food, drink, medication, or supplements.

Use of changes or patterns of changes in health metrics data that occur over time is a very powerful tool that will enable vast improvements in health care methodologies. However, use of changes or patterns of changes is not the only methodology that universal health metrics monitors can utilize for detecting selected adverse health issues. Universal health metrics monitors are also configurable for making selected sensor-observation-enabled health-related determinations using data that was derived at one time (one-time tests). Preferably this type of determination will be made based upon one or more one-time sensor-observations that reliably indicate a selected adverse health-related occurrence has been observed. As an example, dogs are now used to detect that people have abnormal cancer cell counts or that people are infected with COVID-19. Universal health metrics monitors are configurable for utilizing sensor observation data to identify odors or chemical signatures that reliably indicate that people have abnormal cancer cell counts or that people are infected with COVID-19.

Universal health metrics monitors and their one-time tests are universal, therefore universal health metrics monitors are configurable for providing one-time tests regarding any sensor-observable aspects, characteristics, or features of peoples' health from a complete spectrum of one-time, sensor-observable, analytically rich aspects, characteristics, or features of peoples' health. This capability will profoundly change how adverse health occurrences are diagnosed either remotely or in person.

We live in a technologically interconnected world with vast cyber resources. This colossal spectrum of available cyber resources is ever-widening, and over time our technologically interconnected world appears to be destined to provide every possible cyber resource that humanity could ever want or need. When that time comes, the entire body of cyber resources will include and rely heavily upon scalable, configurable, universal, complete spectrum sensor data analyzing machines (such as the scalable, configurable, universal, complete spectrum sensor data analyzing machines disclosed herein) that are configurable for utilizing measure points in their locating of selected analytically rich aspects, characteristics, or features of or from sensor-observation-derived representations in their making of, not only the presently needed 100% accurate cyber determinations regarding the identity of any one specific person, but also every other cyber determination regarding or utilizing sensor observations or sensor observation subjects that our world could ever want, or need.

One skilled in the art will appreciate that some of the methodologies disclosed herein can be implemented utilizing software programs. Such software programs can take the form of suitable programming instructions disposed in tangible, non-transient medium which, when implemented by computer processors, performs all or parts of the methodologies described herein.

While the disclosed sensor data analyzing machines have been defined in terms of their preferred and alternative embodiments, those of ordinary skill in the art will understand that numerous other embodiments and applications of the disclosed analyzing machines will become apparent. Such other embodiments and applications shall be included within the scope and meaning of the disclosure as defined by the appended claims. Moreover, it is to be understood that the above description of the present disclosure is illustrative and is not intended to be limiting. It will thus be appreciated that various additions, substitutions, and modifications may be made to the above described embodiments without departing from the scope of the present disclosure. Accordingly, the scope of the present disclosure should be construed in reference to the appended claims.

What is claimed is:

1. Scalable, configurable, universal, complete spectrum, sensor data analyzing machines;
    said analyzing machines comprise analyzing machine resources that include: (a) computers, (b) tools, (c) methodologies, (d) programming, (e) information, (f) selected criteria, (g) data, and (h) other necessary resources;
    said analyzing machine resources are from a complete spectrum of resources that can be used as parts of analyzing machines, or as parts of analyzing machine operations;
    said analyzing machines, or parts thereof, can be utilized for purposes from a complete spectrum of purposes for which analyzing machines, or parts thereof can be utilized;
    said computers include tangible non-transient memory devices and input devices or output devices;
    said analyzing machines utilize all or parts of said analyzing machine resources for: (a) selecting or deriving data that are included in concise datasets, or (b) utilizing concise datasets in making selected cyber determinations regarding or utilizing sensor observations or sensor observation subjects;
    said analyzing machines utilize said concise datasets in their making of said selected cyber determinations regarding or utilizing sensor observations or sensor observation subjects;
    said concise datasets are utilizable for purposes from a complete spectrum of purposes for which concise datasets can be utilized;
    said concise datasets include selected sensor data or derived data;
    said selected sensor data includes informational representations that were selected from sensor observation datasets;
    said derived data includes informational representations that were derived from processing (i) informational representations that were selected from sensor observation datasets, or (ii) informational representations that were selected from derived data;
    said selected sensor data or said derived data are utilizable by said analyzing machines in their making of said selected cyber determinations regarding or utilizing sensor observations or sensor observation subjects;
    said analyzing machines utilize selected tools, methodologies, or programming for processing said derived data, said tools, methodologies, or programming are from a complete spectrum of tools, methodologies, or programming that can be utilized to derive data for or from concise datasets;
    said analyzing machines are configurable for utilizing measure points in their locating of selected analytically rich aspects, characteristics, or features of or from sensor observation-derived representations of sensor observations or sensor observation subjects;
    said measure points are utilizable by said analyzing machines in their making of said selected cyber determinations regarding or utilizing sensor observations or sensor observation subjects;
    said analyzing machines assign appropriate informational representations to said measure points and to said selected analytically rich aspects, characteristics, or features of or from said sensor observation-derived representations that are located through utilization of said measure points;
    said analytically rich aspects, characteristics, or features of or from said sensor observations or said sensor observation subjects are from a complete spectrum of analytically rich aspects, characteristics, or features of or from sensor observations or sensor observation subjects;
    said analytically rich aspects, characteristics, or features of or from said measure points are from a complete spectrum of analytically rich aspects, characteristics, or features of or from measure points;
    said cyber determinations are from a complete spectrum of cyber determinations that can be made regarding or utilizing sensor observations, sensor observation subjects, or measure points;
    said complete spectrum of cyber determinations regarding or utilizing sensor observations, sensor observation subjects, or measure points includes cyber determinations that identify tells that are utilizable by said analyzing machines in their accurate or reliable making of said selected cyber determinations regarding or utilizing sensor observations, sensor observation subjects, or measure points;
    said tells are from a complete spectrum of sensor-observable tells regarding or utilizing sensor observations, sensor observation subjects, or measure points;
    said selected cyber determinations are utilizable for purposes from a complete spectrum of purposes for which cyber determinations regarding or utilizing sensor observations, sensor observation subjects, or measure points can be utilized;
    said analyzing machines are configurable for making said selected cyber determinations in real time or at times thereafter;
    said analyzing machines are configurable for making at least one member selected from the group consisting of (1) one-time, single event cyber determinations regarding or utilizing sensor observations, sensor observation subjects, or measure points, (2) intermittently provided cyber determinations regarding or utilizing sensor observations, sensor observation subjects, or measure points, and (3) constantly provided cyber determinations regarding or utilizing sensor observations, sensor observation subjects, or measure points;
    said analyzing machines utilize information from a complete spectrum of information that can be utilized by analyzing machines in their selecting, deriving, or processing of data for or from concise datasets, or their making of said selected cyber determinations;

said complete spectrum of information includes information from sensor observations;

said information is from points in time or from over periods of time;

said sensor observations are made by sensors from a complete spectrum of sensors that can be utilized by analyzing machines in their making of selected cyber determinations regarding or utilizing sensor observations or sensor observation subjects;

said analyzing machines are configurable and all or parts of their resource or operations can be configured for utilization in one or more configurations;

said analyzing machines are scalable, in regard to included or utilized analyzing machine resources, to fall at a point in a range of, from a minimum to a maximum, wherein at the minimum, said analyzing machines are scaled to only include or utilize resources that are needed in their making of least complex selected cyber determinations, in regard to included or utilized analyzing machine resources, and wherein at the maximum, said analyzing machines are scaled to include or utilize all analyzing machine resources;

said sensor observations or said sensor observation subjects are from a complete spectrum of sensor observations or sensor observation subjects; and said analyzing machines further comprise and utilize, in any sequence, at least one part of at least one operation from a group consisting of (a) first series observation operations, wherein said analyzing machines are configured for utilizing first series sensor observations, wherein first series sensor observations or subjects of said first series sensor observations have previously determined analytically rich aspects, characteristics, or features, said analyzing machines recognize said previously determined aspects, characteristics, or features, said analyzing machines assign appropriate informational representations regarding said recognized aspects, characteristics, or features of or from said sensor observations or said sensor observation subjects, said assigned informational representations are utilizable by said analyzing machines in their making of selected cyber determinations regarding or utilizing said sensor observations or said sensor observation subjects, said analyzing machines include assigned informational representations of or from said first series observations in first series observation concise datasets, (b) second series observation operations, wherein said analyzing machines are configured for utilizing second series sensor observations, wherein second series sensor observations or subjects of said second series observations have selected yet-to-be-determined analytically rich aspects, characteristics, or features, said analyzing machines recognize said yet-to-be-determined analytically rich aspects, characteristics, or features, said analyzing machines assign appropriate informational representations regarding said yet-to-be-determined analytically rich aspects, characteristics, or features of or from said sensor observations or said sensor observation subjects, said assigned informational representations are utilizable by said analyzing machines in their making of said selected cyber determinations regarding or utilizing said sensor observations or said sensor observation subjects, said analyzing machines include assigned informational representations of or from said second series observations in second series observation concise datasets, (c) measure point operations, wherein said analyzing machines utilize measure points in their locating of selected analytically rich aspects, characteristics, or features of or from sensor observation-derived representations of sensor observations or sensor observation subjects, wherein said analyzing machines assign appropriate informational representations regarding said measure points or said selected analytically rich aspects, characteristics, or features, wherein said informational representations are stored or utilized by said analyzing machines in their making of selected cyber determinations regarding or utilizing sensor observations or sensor observation subjects, (d) concise datasets operations, wherein said analyzing machines select, derive, or utilize data for or from concise datasets, wherein said concise datasets include selected sensor data or derived data, wherein said selected sensor data includes informational representations from sensor observation datasets, and wherein said derived data is comprised of informational representations that were derived from (i) processing of selected informational representation from said sensor observation datasets, or (ii) processing of selected informational representations from said derived data, wherein informational representations from said selected data or said derived data are utilizable by said analyzing machines in their making of selected cyber determinations regarding or utilizing sensor observations or sensor observation subjects, (e) matching operations, wherein said analyzing machines match selected informational representations from second series observation concise datasets to comparable informational representations from first series observation concise datasets, (f) comparing operations, wherein said analyzing machines make comparisons of selected informational representations from second series observation concise datasets to selected informational representations from first series observation concise datasets, wherein said analyzing machines utilize data from said comparisons (i) for providing conclusions, or (ii) in their making of said selected cyber determinations, (g) determining operations, wherein said analyzing machines utilize said conclusions from said comparing operations or said information in their making of selected cyber determinations regarding or utilizing sensor observations or sensor observation subjects, and (h) reporting operations, wherein said analyzing machines make selected reports regarding or utilizing aspects, characteristics, or features of or from their operations.

2. The analyzing machines of claim 1, wherein said analyzing machines are further configured for utilizing: (a) tools, (b) methodologies, (c) programming, (d) people, or (e) combinations thereof for selecting aspects, characteristics, or features of or for operations of said analyzing machines, said tools, methodologies, and programming are from a complete spectrum of tools, methodologies, and programming that can be utilized for selecting aspects, characteristics, or features of or for operations of said analyzing machines.

3. The analyzing machines of claim 1, wherein said analyzing machines are further configured for utilizing at least one member selected from the group consisting of (a) tools, (b) methodologies, (c) programming, (d) data, (e) information, (f) people, and (g) combinations thereof in their making of selected determinations regarding points where selected measure points will be located on sensor observation-derived representations, and wherein at least one member selected from the group consisting of said (a) tools, (b) methodologies, (c) programming, (d) data, (e) information, (f) people, and (g) combinations thereof are utilized for making at least one type of determination selected from the group consisting of:

(i) determinations of where selected measure points will be located on sensor observation-derived representations of only one specific sensor observation subject, (ii) determinations of where selected measure points will be located on sensor observation-derived representations of sensor observation subjects that are members of specific groups of sensor observations subjects, and (iii) determinations of where selected measure points will be located on sensor observation-derived representations of sensor observation subjects that are from a complete spectrum of sensor observation subjects.

4. The analyzing machines of claim 1, wherein said complete spectrum of sensor observation subjects includes people as sensor observation subjects;

wherein analytically rich aspects, characteristics or features of said people include aspects, characteristics, or feature from a complete spectrum of sensor-observable analytically rich aspects, characteristics or features of people;

wherein measure points are utilizable in locating selected analytically rich aspects, characteristics, or features of or from sensor observation-derived representations of people;

said measure points are utilizable for purposes from a complete spectrum of purposes for which measure points that are utilized in locating selected analytically rich aspects, characteristics, or features of or from sensor observation-derived representations of people can be utilized;

said spectrum of analytically rich aspects, characteristics, or features of or from sensor observation-derived representations of people includes sensor observation-derived representations selected from the group consisting of: (a) scars, (b) marks, (c) tattoos, (d) fingerprint features, (e) axis points at joints, (f) tips of noses, (g) corners of eyes, (h) centers of pupils, (i) corners of mouths, (j) tips of fingers, (k) patterns of sweat glands, (l) coughs, (m) tremors, (n) shivers, and (o) voices.

5. The analyzing machines of claim 1, wherein said analyzing machines are further configured for making selected cyber determinations regarding or utilizing said sensor observations or said sensor observation subjects, wherein said sensor observations are made: (a) at points in time, or (b) over periods of time and said analyzing machines include, in concise datasets, informational representations regarding or utilizing selected analytically rich changes that occur over time to sensor-observable aspects, characteristics, or features of or from sensor observation-derived representations of said sensor observations or said sensor observation subjects.

6. The analyzing machines of claim 5, wherein said analyzing machines are further configured for utilizing analytically rich changes that occur over time to sensor observation-derived representations of people, said changes include changes to aspects, characteristics, or features of sensor observation-derived representations of peoples': (a) heads, (b) faces, (c) mouths, (d) eyes, (e) eyebrows, (f) noses, (g) arms, (h) hands, (i) fingers, (j) legs, (k) feet, (l) necks, (m) torsos, (n) skin, (o) hearts, (p) stomachs, (q) intestines, (r) livers, (s) kidneys, (t) lungs, (u) breath, (v) vascular systems, (w) brains, (x) spinal cords, (y) neural systems, (z) neural activities, (aa) skeletons, (bb) blood, (cc) odors, (dd) voices, (ee) movements, (ff) tips of noses, (gg) corners of eyes, (hh) centers of pupils, (ii) axis points at joints, or (jj) aspects, characteristics, or features of sensor observation-derived representations of people from a complete spectrum of other aspects, characteristics, or features of sensor observation-derived representations of people where sensor-observable analytically rich changes occur over time to said representations of said people.

7. The analyzing machines of claim 1, wherein said selected cyber determinations include determinations of any indicated measures of probability that exist of one specific yet-to-be-identified person being the same person as one specific known person, said measures of probability range from making cyber determinations that said one specific yet-to-be-identified person absolutely is not said one specific known person, through making cyber determinations of any intermediate indicated measure of probability that exist of said one specific yet-to-be-identified person being said one specific known person, to making cyber determinations that said one specific yet-to-be-identified person absolutely is said one specific known person.

8. The analyzing machines of claim 1, wherein said analyzing machines are further configured for making selected cyber determinations that are utilized in processes of accurately or reliably granting or denying people or cyber devices access to at least one member selected from the group consisting of: (a) all or parts of said analyzing machines, (b) all or parts of resources that are being utilized by said analyzing machines, and (c) all or parts of resources that are utilizing said analyzing machines.

9. The analyzing machines of claim 1, wherein said analyzing machines are further configured for being utilized for accurately or reliably performing cyber testing of identities of specific people, wherein analyzing machine cyber identity testing can be configured to utilize selected levels of participation by people who are subjects of said cyber identity testing, and said selected levels of participation range from tested people being observable by sensors, but not consciously engaged in said cyber identity testing, to said tested people being observable and consciously engaged participants in said cyber identity testing.

10. The analyzing machines of claim 9, wherein said cyber identity testing is further configured to include repeating operations, wherein parts of first series observations of one specific known person are selected to be repeated by one specific yet-to-be-identified person, wherein said one specific yet-to-be-identified person performs selected repetitions, said analyzing machines assign appropriate informational representations regarding or utilizing at least one member selected from the group consisting of: (a) said observations, (b) said repetitions, and (c) analytically rich aspects, characteristics, or features of or from said one specific yet-to-be-identified person while said yet-to-be-identified person performs said repetitions, wherein said second series observation concise datasets of said repetitions include informational representations that were appropriately assigned to said repetitions by said analyzing machines, and said second series observation concise datasets from said repetitions are utilizable by said analyzing machines in their making of selected cyber determinations regarding said identity of said one specific yet-to-be-identified person.

11. The analyzing machines of claim 1, wherein said analyzing machines are further configured to be utilized, in whole or part, as universal health metrics monitors, said universal health metrics monitors are configurable for monitoring or recording selected parts of sensor observations of selected analytically rich aspects, characteristics, or features of peoples' health;
- said universal health metrics monitors are configurable for making or reporting on selected cyber determination regarding or utilizing selected sensor-observed analytically rich aspects, characteristics, or features of peoples' health;
- said universal health metrics monitors are configurable for making cyber determinations from a complete spectrum of cyber determinations that can be made regarding or utilizing health-related analytically rich aspects, characteristics, or features of or from sensor observation-derived-representations of people;
- said complete spectrum of cyber determinations regarding or utilizing health-related analytically rich aspects, characteristics, or features of or from sensor observation derived-representations of people includes cyber determinations that identify health-related tells regarding or utilizing analytically rich aspects, characteristics, or features of or from sensor observation-derived representations of people, said health-related tells can be utilized by said analyzing machines in their accurate or reliable making of cyber determinations that specific people have, had, or will have selected health-related occurrences that said specific people may, should, or do want to utilize or be made aware of;
- said health-related tells are from a complete spectrum of sensor-observable tells regarding peoples' health;
- said health-related tells are utilizable by said universal health metrics monitors in their making of selected cyber determination regarding or utilizing selected sensor-observed analytically rich aspects, characteristics, or features of peoples' health;
- said selected cyber determinations are utilizable by said universal health metrics monitors in their monitoring of, or their reporting on, selected sensor-observed analytically rich aspects, characteristics, or features of or from peoples' health;
- monitoring operations of or recording operations of said universal health metrics monitors can be made: (a) as one-time, single events, (b) intermittently, or (c) constantly;
- reporting operations of said universal health metrics monitors are configurable for making reports from a complete spectrum of reports that can be made regarding or utilizing health-related analytically rich aspects, characteristics, or features of or from sensor observation-derived representations of people;
- said recordings are made of all or parts of selected sensor observations;
- people or universal health metrics monitors select said all or said parts of said selected sensor observations that are to be recorded or utilized;
- said universal health metrics monitors are configurable for including, in concise datasets, said selected all or said selected parts of said sensor observation datasets;
- said sensor observations are made at points in time or over periods of time;
- said sensors are from a complete spectrum of sensors that can be utilized for observing or recording analytically rich health-related sensor observations of people; and
- said complete spectrum of sensors includes: (i) internal sensors, (ii) external sensors, (iii) wearable sensors, (iv) sensors that are in an observable proximity of people who are subjects of sensor observations, or (v) other sensors that are utilizable in making selected cyber determinations regarding or utilizing peoples' health.

12. The universal health metrics monitors of claim 11, wherein said universal health metrics monitors are configurable for being utilized for making selected one-time, single event, health-related cyber test determinations regarding or utilizing selected sensor-observed analytically rich aspects, characteristics, or features of peoples' health;
- said selected one-time, single event, health-related cyber test determinations are configurable for being made or utilized in real time or at times thereafter;
- said selected one-time, single event, health-related cyber test determinations are made utilizing data from a complete spectrum of data that can be utilized by analyzing machines in their making of one-time, single event, health-related cyber test determinations regarding or utilizing selected sensor-observable analytically rich aspects, characteristics, or features of peoples' health;
- selected analytically rich aspects, characteristics, or features of peoples' health are from a complete spectrum of sensor-observable analytically rich aspects, characteristics, or features of peoples' health;
- a complete spectrum of health-related cyber test determinations regarding or utilizing selected sensor-observable analytically rich aspects, characteristics, or features of peoples' health includes test determinations regarding a presence of: (a) COVID-19, (b) H1N1, (c) Ebola, (d) cancer, or (e) a complete spectrum of other selected aspects, characteristics, or features of peoples' health that can be sensor-observed, tested, and accurately or reliably reported on;
- said one-time, single event, health-related cyber test determinations regarding or utilizing selected sensor-observed analytically rich aspects, characteristics, or features of peoples' health can be utilized for purposes from a complete spectrum of purposes for which one-time, single event, health-related cyber test determinations regarding or utilizing sensor-observed analytically rich aspects, characteristics, or features of peoples' health can be utilized;
- said complete spectrum of purposes for which one-time, single event, health-related cyber test determinations can be utilized includes making health-related cyber test determinations regarding or utilizing sensor-observed analytically rich aspects, characteristics, or features of peoples' health prior to, or immediately prior to tested people being granted or denied access to at least one member selected from the group consisting of: (i) schools, (ii) public transportation, (iii) houses of worship, (iv) workplaces, (v) events, (vi) sporting activities, (vii) restaurants, (viii) bars, (ix) stores, (x) hospitals, (xi) parks, (xii) prisons, (xiii) nursing homes, (xiv) grocery stores, (xv) theaters, (xvi) gyms, (xvii) health care providers' offices, (xviii) concerts, (xix) salons, (xx) meat processing plants, and (xxi) other places or activities where it is required or desired to determine if tested people do or do not have selected health-related aspects, characteristics, or features that would or should exclude specific tested people from gaining access to those other places or activities.

13. The analyzing machines of claim 1, wherein said analyzing machines are further configured for utilizing measure points in their locating of sensor observation-derived representations of selected analytically rich aspects, characteristics, or features of or from sensor observation-derived representations of faces of people;

said measure points are utilized for purposes from a complete spectrum of purposes for which measure points that are utilized in the locating of analytically rich aspects, characteristics, or features of or from sensor-observation-derived representations of faces of people can be utilized;

said complete spectrum of purposes for which measure points that are used in locating selected analytically rich aspects, characteristics or features of or from sensor observation-derived representations of faces of people can be utilized includes utilizing said measure points in the processes of: (a) determining identities of yet-to-be-identified people, (b) authenticating claimed identities of yet-to-be-identified people, (c) determining peoples' facial affects, (d) determining peoples' facial expressions, (e) determining gaze of peoples' eyes, (f) determining sensor or camera angles, (g) determining sensor observation lighting circumstances, (h) determining peoples' poses, (i) determining what portions of peoples' faces are being observed, (j) determining measures of peoples' state of mental or physical health, (k) determining peoples' pulse rates, (l) determining peoples' blood pressure, (m) determining relationships between sensors and measure points that are located on sensor observation-derived representations of peoples' faces, and (n) making determinations from a complete spectrum of other determinations for which measure points that are used in the locating of selected analytically rich aspects, characteristics, or features of or from sensor observation-derived representations of peoples' faces can be utilized.

14. The analyzing machines of claim 1, wherein said analyzing machines are further configured for making selected cyber determinations regarding or utilizing measured locations of, or measured orientations of selected analytically rich aspects, characteristics, or features of or from sensor observation-derived representations of people;

said analytically rich aspects, characteristics, or features of or from said people are from a complete spectrum of sensor observation-derived representations of analytically rich aspects, characteristics, or features of or from people;

measured locations of, or measured orientations of said selected analytically rich aspects, characteristics, or features of or from said sensor observation-derived representations of said people include measured locations of or measured orientations of: (a) sensor observation-derived representations of fingerprint features on sensor observation-derived representation of peoples' fingers, or fingerprints, (b) sensor observation-derived representations of tattoos on sensor observation-derived representations of people, (c) sensor observation-derived representations of scars on sensor observation-derived representations of people, (d) sensor observation-derived representations of marks on sensor observation-derived representations of people, (e) sensor observation-derived representations of patterns of sweat glands on sensor observation-derived representations of people, (f) sensor observation-derived representations of pulse points on sensor observation-derived representations of people, or (g) sensor observation-derived representations of analytically rich aspects, characteristics, or features of people from a complete spectrum of other sensor observation-derived representations of analytically rich aspects, characteristics, or features of people.

15. The analyzing machines of claim 1, further comprising cyber devices;

wherein said analyzing machines are further configured for utilizing measure points in their locating of sensor observation-derived representations of one or more tips of peoples' fingers;

said measure points are utilized for purposes from a complete spectrum of purposes for which measure points that are utilized in locating sensor observation-derived representations of peoples' fingertips can be used;

said complete spectrum of purposes includes utilization of said measure points as components of fingertip-to-cyber device touchless user interfaces; and said cyber devices are types of cyber devices from a complete spectrum of types of cyber devices that can utilize fingertip-to-cyber device touchless user interfaces.

16. The analyzing machines of claim 1, further comprising cyber devices;

wherein said analyzing machines are further configured for using measure points in their locating of selected analytically rich aspects, characteristics, or features from sensor observation-derived representations of people, wherein said measure points can be utilized as components of human-to-cyber device touchless user interfaces;

said human-to-cyber device touchless user interfaces, using said measure points, are utilized for purposes from a complete spectrum of purposes for which human-to-cyber device touchless user interfaces can be utilized; and said cyber devices are types of cyber devices from a complete spectrum of types of cyber devices that can utilize human-to-cyber device touchless user interfaces.

17. The analyzing machines of claim 1, wherein said analyzing machines are further configured for utilizing measure points in their locating of axis points from sensor observation-derived representations of joints of people;

said measure points that locate said axis points are utilized for purposes from a complete spectrum of purposes for which measure points that locate sensor observation-derived representations of axis points of peoples' joints can be utilized; and said complete spectrum of purposes for which measure points that are utilized in locating sensor observation-derived representations of axis points of joints of people can be utilized includes: (a) making selected cyber determinations regarding or utilizing observed geometries of said sensor observation-derived representation of said joints of people, or (b) making selected cyber determinations that utilize said measure points that locate said sensor observation-derived representations of said axis points of said joints of said people for purposes from a complete spectrum of other purposes for which measure points that locate sensor observation-derived representations of axis points of joints of people can be utilized.

18. The analyzing machines of claim 1, wherein said analyzing machines are further configured to be utilized for making selected cyber determinations regarding or utilizing analytically rich aspects, characteristics, or features of observed geometries of sensor observation-derived representation of joints of people; and said selected analytically rich aspects, characteristics, or features of geometries of said sensor observation-derived representations of joints of people are utilized for purposes from a complete spectrum of purposes for which analytically rich aspects, characteristics, or features of observed geometries of sensor observation-derived representations of joints of people can be utilized.

19. The analyzing machines of claim 1, wherein said analyzing machines use measure points in their making of selected measurements;

said selected measurements are from a complete spectrum of measurements that can be made through use of measure points that are utilized in locating selected analytically rich aspects, characteristics, or features of or from sensor observation-derived representations; and said complete spectrum of measurements that can be made through use of said measures point includes: (a) measured distances between measure points, (b) measured angles where lines between measure points meet or intersect, (c) measured locations of measure points, aspects, characteristics, or features, (d) measured orientations of measure points, aspects, characteristics, or features, (e) measured relationships between measure points, aspects, characteristics, or features, (f) time of capture of sensor observations or parts thereof, (g) measured pressures at or in areas of measure points, (h) measured temperatures at or in areas of measure points, (i) measured levels of colored light at or in areas of measure points, (j) measured grey scale levels at or in areas of measure points, (k) measured odors at or in areas of measure points, (l) measured presences at or in areas of measure points, (m) measured sound at or in areas of measure points, (n) measured energy at or in areas of measure points, (o) measured chemicals presence at or in areas of measure points, or (p) measures of sensor-observable analytically rich aspects, characteristics, or features from a complete spectrum of other measurable sensor-observable analytically rich aspects, characteristics, or features of or from sensor observation-derived representations that can be located or reported on through utilization of measure points.

20. The analyzing machines of claim 1, wherein said analyzing machines are configurable for performing analyzing machine operations, or parts thereof, in any usable order or sequence.

21. The analyzing machines of claim 1, wherein said analyzing machines are further configured to achieve selected attainable level of accuracy goals for selected cyber determinations and said attainable level of accuracy goals fall in a range extending from 0% accuracy, and goes up to, and includes, 100% accuracy.

22. The analyzing machines of claim 1, wherein said analyzing machines are further configured for utilizing information or informational representations from sources that are not first series observation operations or second series observation operations.

23. The analyzing machines of claim 1, wherein said analyzing machines are further configured for manipulating, in possible ways, operations of analyzing machine utilized resources or operations of said analyzing machines, said manipulating provides said analyzing machines with selections of possible utilizations, said manipulating is utilized for purposes from a complete spectrum of purposes for which said manipulating can be utilized, said complete spectrum of purposes for utilizing said manipulating includes a purpose of aiding said analyzing machines in their making of selected cyber determinations.

24. The analyzing machines of claim 1, wherein all or part of sensor observation datasets from sources that are not first series observation operations are included as all or part of first series observation concise datasets, and all or part of sensor observation datasets from sources that are not second series observation operations are included as all or part of second series observation concise datasets.

25. The analyzing machines of claim 1, wherein said analyzing machines are further configured to include analyzing machine history, said analyzing machine history is comprised of analyzing machine history records, and said analyzing machine history records are utilizable for purposes from a complete spectrum of purposes for which analyzing machine history records can be utilized.

26. The analyzing machines of claim 1, wherein said analyzing machines are further configured to derive or utilize information from points in time or from periods of time, from a complete spectrum of information that includes information regarding observed analytically rich aspects, characteristics, or features of or from sensor observations or subjects of sensor observations, thereby obtaining sensor-derived information;

said sensor observations are types of sensor observation from the group consisting of (a) visual sensor observations, (b) audible sensor observations, (c) thermal sensor observations, (d) olfactory sensor observations, (e) tactile sensor observations, (f) chemical sensor observations, or (g) types of sensor observations from a complete spectrum of other types of sensor observations that can be utilized by said analyzing machines;

said analyzing machines capture, select, derive, or utilize data for or from concise datasets, or make selected cyber determinations through utilization of (a) tools, (b) methodologies, (c) programming, (d) computers, (e) sensor data, (f) said information, (g) criteria that are utilized by said analyzing machines, and (h) other necessary resources;

said analyzing machines make at least one type of cyber determination selected from the group consisting of (i) one-time, single event cyber determinations, (ii) intermittently made cyber determinations, and (iii) constantly made cyber determinations;

said selected cyber determinations are utilized for purposes from a complete spectrum of purposes for which cyber determinations regarding or utilizing sensor observations or sensor observation subjects can be utilized; and said analyzing machines further comprise utilizing at least one part of at least one operation selected from the group consisting of (a) first series observation operations, wherein said analyzing machines utilize sensor observations, wherein said sensor observations or subjects of said sensor observations have previously determined aspects, characteristics, or features, said analyzing machines recognize said aspects, characteristics, or features, said recognized aspects, characteristics, or features are utilizable by said analyzing machines in their making of selected cyber determinations, said analyzing machines assign appropriate informational representations regarding selected known aspects, characteristics, or features of said sensor observations or said sensor observation subjects, said analyzing machines include all or parts of said informational representations in first series observation concise datasets,
(b) second series observation operations, wherein said analyzing machines utilize sensor observations, and wherein said sensor observations or subjects of said sensor observations have selected yet-to-be-determined aspects, characteristics, or features, said analyzing machines recognize said selected yet-to-be-determined aspects, characteristics, or features, said analyzing machines assign appropriate informational representations regarding said selected yet-to-be-determined aspects, characteristics, or features of said sensor observations or said sensor observation subjects, said analyzing machines include all or parts of said informational representations in second series observation concise datasets,
(c) measure point operations, wherein said analyzing machines utilize measure points in their locating of selected analytically rich aspects, characteristics, or features of or from sensor observation-derived representations of sensor observations or sensor observation subjects, said analyzing machines assign appropriate informational representations regarding said measure points, aspects, characteristics, or features of or from said sensor observation-derived representations, wherein all or parts of said informational representations are stored or utilized by said analyzing machines in their making of selected cyber determinations regarding or utilizing said sensor observations or said sensor observation subjects,
(d) concise datasets operations, wherein said analyzing machines utilize concise datasets in their making of selected cyber determinations, said concise datasets include selected sensor data or derived data, wherein said selected sensor data comprises informational representation that were selected from sensor observation datasets and said derived data comprises informational representation that were derived from (i) processing selected informational representations from sensor observation datasets, or (ii) processing selected informational representations from derived data, said informational representations from said selected sensor data or said informational representations from said derived data are utilizable by said analyzing machines in their making of selected cyber determinations regarding or utilizing sensor observations or sensor observation subjects, and said derived data are derived utilizing tools, methodologies, or programming from a complete spectrum of tools, methodologies, or programming that can be utilized in deriving informational representations from sensor data, or from or for derived data,
(e) matching operations, wherein said analyzing machine matching operations include matching informational representation from second series observation concise datasets to comparable informational representation from first series observation concise datasets,
(f) comparing operations, wherein said analyzing machine comparing operations include comparing informational representation from second series observation concise datasets to comparable informational representation from first series observation concise datasets and providing conclusions or determinations from said comparing,
(g) determining operations, wherein said analyzing machines utilize conclusions or determinations from comparing operations, or information in their making of said selected cyber determinations, and reporting operations, wherein said analyzing machines include reporting operations, wherein said analyzing machines provide selected reports regarding or utilizing selected aspects, characteristics, or features of or from all or parts of cycles of utilization of said analyzing machines.

* * * * *